United States Patent [19]

Choay et al.

[11] Patent Number: 4,987,223

[45] Date of Patent: Jan. 22, 1991

[54] DERIVATIVES OF THE URONIC ACID

[75] Inventors: Jean Choay, Paris; Jean-Claude Jacquinet, Orleans-La-Source; Maurice Petitou, Paris; Pierre Sinay, Orleans, all of France

[73] Assignee: Choay S.A., Paris, France

[21] Appl. No.: 453,731

[22] Filed: Oct. 27, 1982

[30] Foreign Application Priority Data

| Dec. 23, 1981 | [FR] | France | 81 24132 |
| Jan. 15, 1982 | [FR] | France | 82 00621 |
| Feb. 1, 1982 | [FR] | France | 82 01575 |
| Feb. 16, 1982 | [FR] | France | 82 02526 |
| May 28, 1982 | [FR] | France | 82 09392 |
| Jun. 22, 1982 | [FR] | France | 82 10891 |
| Jun. 22, 1982 | [FR] | France | 82 10892 |
| Aug. 6, 1982 | [FR] | France | 82 13804 |
| Sep. 20, 1982 | [FR] | France | 82 15803 |
| Sep. 20, 1982 | [FR] | France | 82 15804 |
| Oct. 27, 1982 | [FR] | France | 82 18001 |

[51] Int. Cl.$^5$ .................. C07H 3/00; C07H 13/00; C07H 15/00

[52] U.S. Cl. .................. 536/17.7; 536/1.1; 536/4.1; 536/17.9; 536/18.2; 536/18.5; 536/18.6; 536/115; 536/119; 536/122; 536/124

[58] Field of Search .............. 549/414, 417; 536/1.1, 536/4.1, 18.2, 18.5, 18.6, 124, 115, 119, 122, 17.7, 17.9

[56] References Cited

U.S. PATENT DOCUMENTS

| 2,650,237 | 8/1953 | Couch et al. | 536/124 |
| 2,798,079 | 7/1957 | Linn | 260/345.7 |
| 2,845,439 | 7/1958 | Reiners | 536/18.2 |
| 2,938,900 | 5/1960 | Walton | 536/4.1 |
| 2,985,664 | 5/1961 | Krebs et al. | 536/4.1 |
| 3,356,674 | 12/1967 | Ikeda et al. | 536/4.1 |
| 3,632,802 | 1/1972 | BeMiller et al. | 536/18.5 |
| 3,959,253 | 5/1976 | Jones | 536/4.1 |
| 4,107,425 | 8/1978 | Pfeffer et al. | 536/18.2 |
| 4,238,473 | 12/1980 | Lemieux et al. | 536/116 |
| 4,316,983 | 2/1982 | Bollag et al. | 536/18.2 |
| 4,335,236 | 6/1982 | Tsuyumu et al. | 536/18.2 |
| 4,424,348 | 1/1984 | Rubin | 536/4.1 |
| 4,442,284 | 4/1984 | Kolar et al. | 536/4.1 |
| 4,464,531 | 8/1984 | Atsumi et al. | 536/17.4 |

OTHER PUBLICATIONS

Watabe et al., "Chem. Pharm. Bull.", vol. 18, 1970, pp. 414–415.
Bollenback et al., "Jour. Amer. Chem. Soc", vol. 77, 1955, pp. 3310–3315.
Anghileri et al., "Oncology", vol. 25, pp. 19–32, 1971.
Vol. 247, No. 9, 5/1972, pp. 2650–2651, Wang et al., "Jour. Biol. Chem".
Kaneko et al., "Chem. Phar. Bull", vol. 25, 1977, pp. 2458–2460.
Mitchell, "Radiotracer Tech. Appl.", vol. 2, 1977, pp. 1081–1110.
Kiss et al., "Tetrahedron", vol. 32, 1976, pp. 1399–1402.
Srivastava et al., "Carbohydrate Research", vol. 60, 1978, pp. 315–326.
Schmidt et al., "Tetrahedron Letters", vol. 26, 1980, pp. 1421–1424.
Tomasic et al., Chemical Abstracts, vol. 79 (1973), No. 115820n.
Kovac, Chemical Abstracts, vol. 80 (1974), No. 48290y.
Hirsch et al., Chemical Abstracts, vol. 82 (1975), No. 125545f.
Kiss and Wyss, "Tetrahedron", vol. 32, 1976, pp. 1399–1402.
Srivastava et al., "Carbohydrate Research", vol. 60, 1978, pp. 315–326.
Schmidt and Rucker, "Tetrahedron Letters", vol. 26, 1980, pp. 1421–1424.

*Primary Examiner*—Johnnie R. Brown
*Assistant Examiner*—Elli Peselev
*Attorney, Agent, or Firm*—Davis Hoxie Faithfull & Hapgood

[57] ABSTRACT

The invention relates to derivatives with a uronic acid structure having substituents selected among a reactive group, a functionalisable group and —OH functions blocked by protective groups. These derivatives are useful for preparing glycosides, particularly enzyme substrates.

6 Claims, 14 Drawing Sheets

Fig. 3.
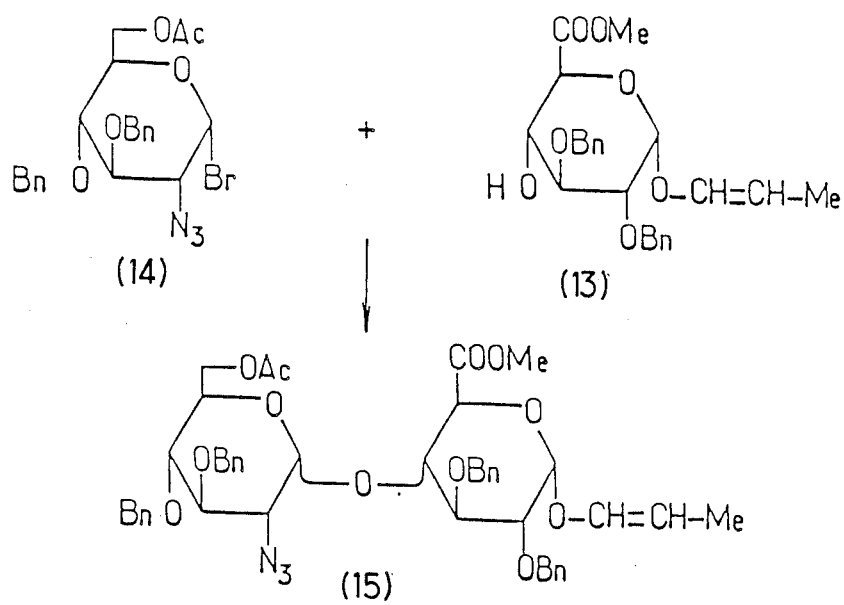
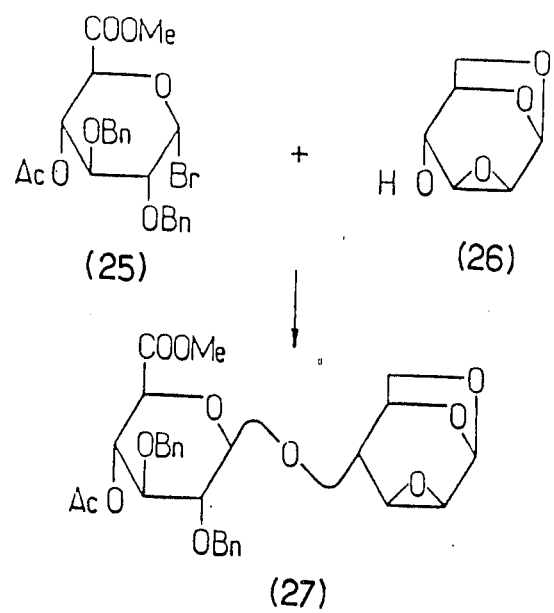
Fig. 5.

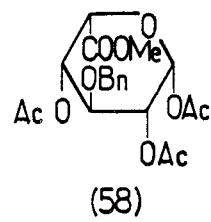 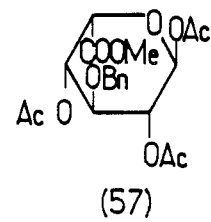
(58)  (57)
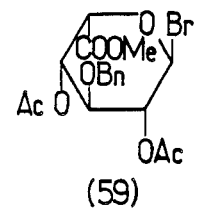
(59)
Fig.10.
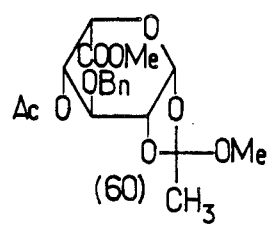 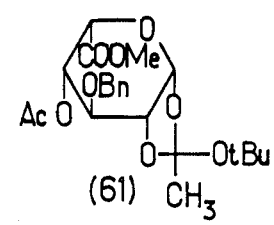
(60)  (61)
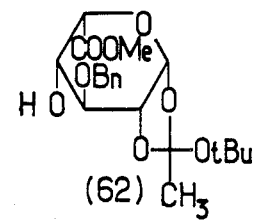 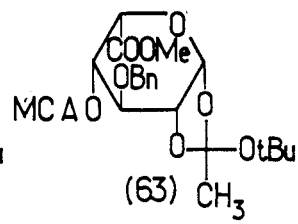
(62)  (63)

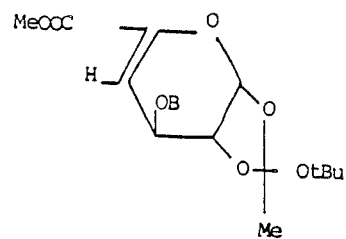
composé (64)
Fig.11.
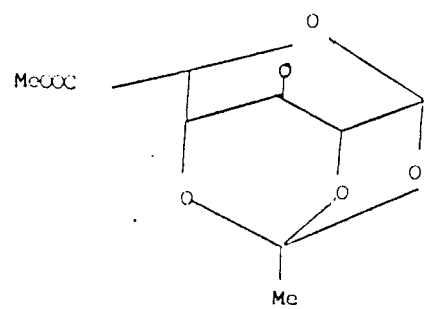
composé (65)
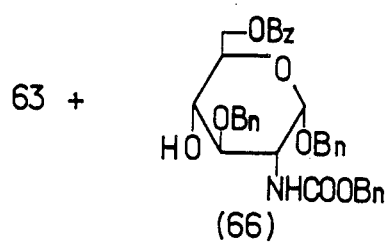
63 +
(66)
Fig.12.
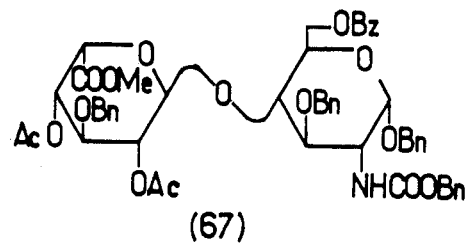
(67)

DERIVATIVES OF THE URONIC ACID

FIELD OF THE INVENTION

The present invention relates to novel derivatives with a uronic acid structure and to the process for their synthesis.

It relates also to the uses of these derivatives, particularly as intermediates of osidic synthesis, enzyme substrates, haptenes and laboratory reagents.

The invention relates more particularly to derivatives of D-glucuronic acid and L-iduronic acid epimers.

It will be recalled that these epimers correspond respectively to the following formulae:

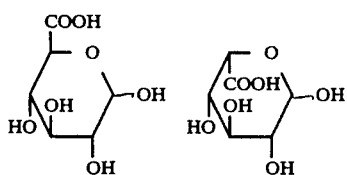

Uronic moieties having said structures enter into the constitution of the osidic chains of biological active compounds of great importance.

Such moieties are particularly present in various natural mucopolysaccharides such as heparin, heparane sulfate, chondroitines and others.

DESCRIPTION OF PRIOR ART

Many works have been done by the applicant to find means enabling oligosaccharides corresponding to fragments of mucopolysaccharides such as those above defined or corresponding to derivatives of these fragments to be synthetically obtained.

The research carried out in that respect has particularly shown, as regards moieties with uronic structure, that certains type of protective groups are necessary to confer to a determined position sufficient reactivity in order to involve it, for example, in a glycosylation reaction and/or to specifically introduce at given positions selected substituents.

Now, regarding more particularly L-iduronic acid structures, only few examples of derivatives have been disclosed in the literature, i.e. more especially by KISS and WYSS in Tetrahedron, volume 32, pp. 1399–1402 1976 and Srivastava et al in Carbonydrate Research 60(1978) 315–326.

Furthermore, low yields and unreproducible results are obtained by the selective oxidation method used for synthesizing these derivatives.

It will be appreciated that such a method cannot be used to bind L-iduronic acid moieties to high costs compounds.

Actually, the activation of the synthesized uronic derivatives to be able to involve them in a glycosylation reaction as glycosylating agents has not been forecast.

The inventors have then been led to undertake research for means enabling easy access to the D-glucuronic acid and L-iduronic acid structures as such and to the desired derivatives, in order to have suitable moieties, particularly for the above mentioned synthesis.

It was hence an object of the invention to provide novel derivatives of D-glucuronic acid and L-iduronic acid endowed with sufficient reactivity enabling them to be involved in glycosylation reactions, as glycosylating agents or as glycosylated agents (in this case, playing the role of an aglycone according to usual terminology).

It was also an object of the invention to provide novel derivatives enabling, through the nature of their protective groups, the introduction specifically, at given positions, of selected substituent groups.

It is aimed, in addition, at providing novel derivatives endowed with sufficient reactivity to enable them to be engaged in glycosylation reactions as glycosylating agents or as glycosylated agents and permitting, due to the nature of their protective groups, the introduction, specifically at given positions, of selected substituent groups.

It was also an object of the invention to provide means enabling the formation of the structures of the acids concerned, in particular that of L-iduronic acid and easy access to the above reactive derivatives for the development of glycosides useful as biological reagents, particularly as enzyme substrates and/or laboratory reagents.

It is directed also at the uses of these derivatives for preparing antigenic determinants wherein conjugated to agents with a high molecular weight, they can induce in animals the formation of antibodies directed against them.

It is also directed at the uses of these conjugates for making immunoabsorbents particularly useful for purifying the above antibodies or any other substance having an affinity for them.

The derivatives of the invention have a uronic acid structure of the formula (III):

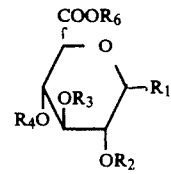

wherein —$OR_1$ to —$OR_6$ are selected among:

a reactive group, i.e. an activator group enabling said uronic acid derivative to be used in a glycosylation reaction as glycosylating agent or as glycosylated agent, such as an halide, particularly a bromide or a chloride, an —O— imidoyl group, an orthoester group together with an adjacent substituent, or again an hydrogen atom;

a functionalisable group constituting the beginning of a conjugatable arm, such as an —O-alkenyl group particularly an —O-allyl, or said conjugatable arm itself, under a protected form, the —OH functions being blocked by protective groups, identical or different from one another, compatible with one another and with the one or more reactive groups and inert with respect to reactions in which, if necessary, it may be desired to involve the monosaccharide, these groups being advantageously, selected amongst the aliphatic or aromatic radicals, particularly in the group comprising an alkyl radical with 1 to 4 carbon atoms, particularly a methyl group, an unsubstituted alkyl radical such a benzyl radical, an acyl radical such as acetyl, benzoyl, chloracetyl, or an alkenyl radical with to 4 carbon atoms such as allyl or vinyl, or the salts of those derivatives, with the exclusion of methyl (benzyl 2,3-di-O-benzyl$\alpha$, $\beta$-L-idopyranosid) uronate and the proviso that in D-glucuronic compounds having a reactive group as above mentioned, $R_2$, $R_3$ and $R_4$ cannot be all three together identical and $R_1$ and $R_4$ be different from a methyl group (this group being removable with difficulty).

It will be noted that the derivatives of the invention with an iduronic structure comprise semi-open derivatives and open derivatives.

The term semi-open derivative designates a derivative activated or potentially activable on a given position.

A derivative semi-open on the right is a derivable able to be engaged by its 1-position in a reaction with another compound.

A derivative semi-open on the left comprises only one free function, more especially only one free —OH group capable to be engaged in a reaction.

An open derivative is semi-open on the right and on the left and therefore can be used as glycosylating agent or asglycosylated agent, as the case may be.

Such derivatives then contain a temporary protective group, that is to say removable independently of the other protective groups present, by recreating an alcohol.

The derivatives of the invention with a glucuronic structure are open.

According to another advantageous feature of the invention, the protective groups $R_2$ and $R_3$, and optionally $R_4$ are different and removable sequentially without alteration of the uronic structure and of the carboxyl function. This feature has the advantage, in the course of subsequent reactions, of being able to introduce in place of all these protective groups of substituents different from one another or alternatively the introduction of only one or several substituents and the liberation of the —OH groups of the remaining positions.

In preferred derivatives of the invention, the reactive group occupies the 1 position.

In other preferred derivatives, the reactive group is at the 4 position.

A preferred family of derivatives of the invention corresponds to the derivatives of D)glucuronic acid of the formula (IV):

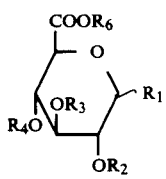
(IV)

in which:
—$R_1$ represents a reactive group selected from among:

1. an activator group enabling the glucuronic derivative to be engaged in a glycosylation reaction as glycosylating agent such as a halide, in particular a chloride or a bromide, a —O-imidoyl group, an orthoester group conjointly with $R_2$:
2. a functional or functionalisable group such as a —O-alkyl substituted radical, or —O-alkenyl such as —O-allyl, said functional or functionalisable group being optionally protected; or
3. a —OH group; —$R_2$ to $R_4$, identical or different, represent a protective group such as an alkyl radical of 1 to 3 carbon atoms, in particular methyl, substituted alkyl, such as benzyl, acyl such as acetyl, benzyl or chloroacetyl, or alkenyl, such as allyl or vinyl;

$R_6$ represents an aliphatic or aromatic radical, in particular an alkyl radical of 1 to 4 carbon atoms or substituted alkyl such as benzyl, and the salts thereof with the exclusion of the above defined D-glucuronic acids.

In a preferred group of derivatives of uronic acid, $R_4$ represents a temporary group forming an ester or an ether with the —OH group that it protects and is selected from among the radicals of the monochloroacetyl, acetyl, benzyl or p-methoxybenzyl, allyl or vinyl type or the like.

Preferred products of this group contain an $R_1$ group representing an O-allyl or O-vinyl group. Such products have the advantage of bearing at the 1 and 4 positions substituents which can be selectively eliminated without however altering the groups at the 2, 3 and 6 positions.

In another preferred group, $R_1$ represents a hydrogen atom, which permits the introduction if desired, at the 1 position, of a reactive group such as a halide or an imidate, or again the production of a glycosylation reaction.

In another preferred group, $R_1$ represents an activator group such as defined above, which permits the monosaccharide to be engaged, for example in a glycosylation reaction.

Another preferred group of products contains a $R_4$ group representing a hydrogen atom, $R_1$ then representing advantageously a functionalisable group such as defined above.

In these various groups $R_2$ and $R_3$ may be identical and represent, for example an acyl group, particularly a benzyl group.

Alternatively, they may different from one another.

Another preferred family of derivatives of the invention corresponds to the derivatives of L-iduronic acid of the formula (V):

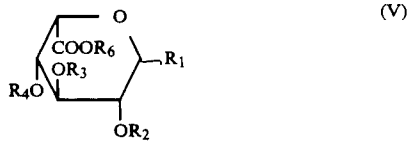
(V)

in which the substituents have the general meanings given above with respect to formula (III).

In a preferred group of L-iduronic acid derivatives, $R_1$ and $R_2$ represent an orthoester.

In another preferred group, $R_1$ represents an activator group such as a halide.

In yet another preferred group, $R_1$ represents an O-alkyl or O-alkenyl radical.

Preferred products of these groups contain advantageously a temporary group at the 4 position.

Other particularly preferred products of these groups contain in addition different substituents $R_2$ and $R_3$, which permits in the course of subsequent operations to submit these groups to different treatments and thereby the introduction of different substituent groups on the unit.

In the case where, for example, $R_2$ represents an acyl group such as acetyl group and $R_2$ a benzyl group, it is possible to introduce at the 2 position a sulphate group in place of the acetyl group, then to free at the 3 position the —OH radical blocked by the benzyl group.

One thus has advantageously available a constituent unit of heparine or of haparane-sulphate chains.

Other preferred products contain substituents, $R_2$ and $R_3$ different from one another.

The invention is also directed to a process of synthesis of these derivatives.

According to this process, there is introduced on to a monosaccharide with uronic structure protective groups compatible with one another, enabling the selective treatment of a given position on which it is desired to introduce a reactive group or, if necessary a given protective group.

A group will be called intermediate protective group if used during the processing of synthesis and then eliminated for the placing in position of a reactive group or of a final protective group, that is to say corresponding to the desired protective group on the monosaccharide of the invention.

It is possible to introduce, from the start, one or several final protective groups.

Alternatively, the introduction of one or several intermediate protective groups enables, in a first stage, a given position to be treated, then when the desired group has been introduced in this position, the treatment of the one or more of the positions occupied by this or these intermediate groups and, as the case may be, successively, for the purposes of the introduction of different final protective groups.

For example, to prepare a monosaccharide comprising a vinyl group, an allyl derivative is advantageously formed in which all the —OH groups of the alcohol functions are blocked by the final protective groups or, as the case may be, intermediate protective groups. This allyl monosaccharide is subjected to the action of an alkylation agent in order to block the —OH group of the carboxyl function. The monosaccharide with an allyl group so protected is then subjected, for example, to the action of a rhodium complex, in the presence of diazabicyclooctane which leads to the corresponding vinyl ether.

It will be noted that in the case where a temporary group has been introduced at a given position, it is then possible to remove this temporary group and to reform at this position an alcohol useful for a glycosylation reaction whilst the vinyl group may be, in its turn, subjected to one or several reactions to lengthen the chain.

From a protected 1-O-vinyl derivative, it is possible, for example, to form a reactive group such as an imidate. To this end, the vinyl derivative is advantageously subjected to the action of mercuric derivatives such as mercuric oxide and mercuric chloride which permits the recreation of an alcohol which is then subjected to the action of an imidoylation agent such as trichloroacetonitrile.

It is also possible to obtain an imidate from an 1-O-hydroxylated derivative obtained by acid hydrolysis of glycoside and in particular of a methylglycoside.

Conventionally, the monosaccharides with a halogenated uronic structure are advantageously obtained by the action of a halogenation agent on an acyl group, itself obtained, as the case may be, by acylation of an alcohol. It is possible to obtain them by the action of the Vilsmeir reagent on a derivative hydroxylated at the 1 position.

It is also possible to prepare a monosaccharide including an orthoester group by operating advantageously from a corresponding halogenated derivative. According to a preferred method of preparation, the halogenated derivative is subjected, in the presence of a proton acceptor such a sym-collidine, to the action of an alcohol.

According to an advantageous feature of the invention, the monosaccharides with L-iduronic structure are prepared from methyl 3-O-benzyl-L-iduronate itself formed from a derivative of D-glucofuranoside type by proceeding as follows.

α-D-glucofuranoside of the following formula (VI) is utilised

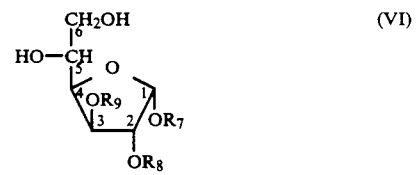

in which the $R_7$ and $R_9$ groups, which may be identical or different from one another, represent a blocking group. In particular $R_7$ and $R_8$ form an isopropylidene group and $R_9$ a benzyl group.

The monosaccharide of formula VI is treated so as to act selectively on one or other of the —OH groups at the 5 or 6 position, in order to obtain the passage from a D-gluco structure to an L-ido structure at the 5 position and the passage from a primary alcohol structure to a carboxylic acid structure at the 6 position.

Rearrangement of the furanose form into the puranose from then follows.

The selective treatment of the —OH groups of the α-gluco chain and the use of the chain formed to pass from the glucofuranoside ring to the idofuranoside ring and then the idopyranoside ring are carried out as follows.

The —CH$_2$OH and —CHOH groups respectively at the 6 and 5 positions are successively converted as follows:

1—conversion from —CH$_2$OH to —CH$_2$OTr, where Tr represents a trityl group. The starting α-glucofuranoside VI is treated to block selectively the —OH group at the 6 position. To this end, it is advantageous to operate with trityl chloride or the like, 2—conversion from —CHOH to —CHOR$_{10}$ where $R_{10}$ is a blocking group. A preferred blocking group corresponds to the case where $R_{10}$ represents a benzoyl group. For its introduction, benzoyl chloride is used.

3—conversion from —CH$_2$OTr to —CH$_2$OH. The deblocking of the hydroxyl group is advantageously effected with paratoluenesulphonic acid, or again with a solution of boron trifluoride in methanol or the like.

4—conversion from —CH$_2$OH to —COOH. For this step a reagent is used enabling passage to the carboxylic acid form. This conversion is advantageously effected by using a solution of chromic oxide in sulphuric acid.

5—conversion from —CHOBz to —CHOH. The product previously obtained is treated with soda. It is then converted to the acid form. To remove the cations, a cation exchange acid resin is used with advantage.

6—conversion from —COOH to —COOMe, where Me represents a methyl group. Esterification is carried out conventionally, by the action particularly of diazomethane.

7—conversion from —CHOH to —CHOTf, where Tf represents the triflyl group. At the 5 position a very reactive group is introduced, such as tosylate, a mesylate or preferably a triflyl group. The reaction with triflic anhydride is then carried out.

8—conversion from —CHOTf to —CHOTFA, TFA representing the trifluoroacetate group (with inversion of the configuration of the carbon at the 5-position). A nucleophilic substitution is carried out with the Walden inversion. This reaction is advantageously effected with sodium trifluoroacetate.

9—conversion from —CHOTFA to —CHOH. The product is treated with methanol and then advantageously chromatography for purification purposes follows.

10—rearrangement of the ring. With advantage an acid medium is employed, in particular, in the presence of trifluoroacetic acid. A mixture of trifluroacetic acid/water of the order of 9/1 is found to be specially suitable.

The invention is directed also as intermediate products, to the furanosides with the D-gluco and L-ido structure and the idopyranosides obtained at the end of steps 2 to 8 above.

As regards more particularly the compound at the L-iduronic acid structure of formula VI obtained in which $R_1$ represents an alkyl group, in particular methyl, it will be noted that it may be saponified and then subjected to a catalytic hydrogenation reaction for the purposes of producing an L-iduronic acid unit.

This compound may be also acylated, converted in the halide and then into the ortho-ester. The protective group at the 4 position can be removed thus enabling the introduction of another temporary protective group at the 4 position.

By means of a suitable choice of the protective group at the 4 position, and according to the nature of the ortho-ester, it is possible, from these compounds of structure VI, to carry out a glycosylation reaction followed by selective removal of the protective group at the 4 position; this position can thus be engaged in another glycosylation reaction.

Finally, the ester or acyl group formed at the 2 position in the course of the first glycosylation reaction can be removed, thus regenerating an —OH function which can be sulphated, if desired.

According to another embodiment, a monosaccharide of the L-idose is prepared possessing at the 1, 2, 3 and 4 positions the desired protective groups; then without altering the protective groups above, the primary alcohol function remained free at the 6 position is chemically oxidised and converted into carboxylic acid group.

The monosaccharides with the D-glucuronic structure are more especially developed from derivatives of glucose by using conventional methods for the introduction of the desired groups.

It will be noticed that in this synthesis the conversion from a D-glucostructure to a L-ido structure, at the methylester acid step, is obtained according to the invention by using a triflate group and sodium trifluoroacetate and enables the desired inversion at the methylester step.

At that time, these conditions are the only one enabling said reaction to be carried out.

With respect to the methods used up to now, the means used according to the invention for obtaining the above defined derivatives, particularly those with a L-iduronic structure, are advantageously easy to carry out and give reproducible results.

Due to the great flexibility of these means it is hence possible to access to derivatives of uronic structure capable of giving rise to various types of chains with a preferred stereochemistry due to their reactivity. In addition, according to the type of protective groups selected, it is possible after engagement in a given type of reaction to selectively introduce in their place given substituent group and/or to liberate one or several —OH groups.

It is thus possible to have oligosaccharides comprising uronic units, substituted specifically such as encountered, for example, in the above biologically active molecular chains.

In this respect, the easy access to a derivative of a 2-O-sulphate-L-iduronic acid derivatives will be more particularly appreciated, which is the substrate of L-iduronatic sulfatase enzyme.

The recent obtention by a synthesis route by the applicant by D-glucuronic acid sulfatation give means for synthesizing sulfated derivatives of this acid, useful as enzyme substrates.

Such synthesis are made possible thanks to the set of protective groups above mentioned.

The invention is also directed at the application of the uronic acid derivatives of the invention to the synthesis of glycosides having a biological interest such as the enzyme substrates of the family of the glucosidases.

Such glycosides are obtained for example by condensing the derivatives of the invention with para-nitro phenol or methylumbelliferone or their derivatives.

For this purpose, a reaction such as the Koenigs-Knorr reaction, well known by the man of the art, can be used, in which an oside halide is contacted with the aglycon to which it is desired to bind the oside, in the presence of an agent fixing the halohydric acid which is formed.

Regarding the iduronic acid, it will be particularly noted that the glycosidic binding is created while the uronic acid structure is already elaborated.

This feature enables glycosylation of products or substances such as protein or solid supports which could not support the synthesis steps of the process of the prior art mentioned above in which the glycosidic binding is formed before elaborating the iduronic acid structure.

The enzyme substrates developed from the monosaccharides of the invention, enable advantageously the study of the specificity of various enzymes, in particular, those degrading heparin particularly the specificity of L-iduronidase, D-glucuronidase and L-iduronate sulfatase.

The glycosides obtained by fixing the monosaccharides of the invention, for example, on methyl umbelliferone, constitute valuable compounds as substrates useful in fluorescence.

In other applications, the monosaccharides of the invention are used for the development of radioactive substrates. These substrates may be obtained by applying a radioactive starting glycoside or by reducing the nitro-phenyl-glycoside groups mentioned above, for the studies of enzymes, to an amine group, then subjected, for example, to an acetylation reaction with tritiated acetic anhydride, using the usual technics.

The interest of having a derivative already having the uronic acid structure will be again noted. It will be measured indeed how important it is to reduce as far as possible the step numbers to which the radioactive compound must be submitted for elaborating a given glycoside, in view of its high cost.

According to another aspect of the invention of great interest, the monosaccharides containing a functionalisable group on the anomeric carbon open the route to the introduction of chains capable of playing the role of anchoring arms useful in various biological applications.

According to still another aspect, glycosides are transformed into anchoring arms when possible and enable fixation through those arms to a protein and thereby the obtaining of artificial antigens.

For this purpose, a glycoside, such as the uronic derivative of para-nitro-glycoside above mentioned, is submitted to a reduction reaction thus leading to the corresponding para-amino-phenyl glycoside, which is then engaged, through an usual diazoic coupling reaction, in a linkage involving the aromatic and particularly the tyrosine moiety of proteins.

Such antigens are used in animals to induce the formation of antibodies which can be purified and used as imimunological reagents.

It is thus possible to develop, from a glycoside as above mentioned or from a functionalisable substituent of an uronic acid derivative various anchoring arms comprising particularly (1) an alkyl radical of 2 to 10 carbon atoms, comprising at the chain end a —OH group, if necessary protected or engaged in a functional group (2) an alkenyl radical comprising from 2 to 10 carbon atoms, Chains of the type (1) correspond advantageously to radicals: alkylene-glycol, α, β-dihydroxypropyl, or β-hydroxyethyl, γ-hydroxypropyl and are useful for the constitution of biological reagents.

The chains (1) and (2) above advantageously contain in addition one or several ether and/or intercalary amine and/or functional terminal group comprising nitrogen such as an amine function or a terminal ether, carboxyl or aldehyde group.

Chains with an amino termination which are particularly preferred are of the alkoxy-alkylamine type in which the alkoxy and alkyl groups contain altogether from 3 to 5 carbon atoms, preferably from 4 to 10, advantageously of the order of 10.

Such chains are advantageously obtained from the allyl derivatives of the invention, according to the process disclosed in U.S. patent application Ser. No. 184,251 in the name of Agence Nationale de Valorisation de la Recherche.

The reactivity of this group permits, in fact, the application of a large number of reactions and, thereby, the obtaining of chains of modulable length and nature, with a hydrophilic character valuable for biological applications.

For lengthing the chain, recourse is had to the conventional reactions of organic synthesis, which will be easily employed by the technicians skilled in the art as a function of the desired chain.

It is for example possible to obtain a chain terminated by an alcohol functional group, in particular, by ozonolysis of the double bond of the allyl group, then to resort to tosylation and, finally, to cause the tosylated derivative to react with an azide.

The azide obtained has a double interest. It is on the one hand a stable compound. On the other hand, by reduction, by conventional techniques, it enables the production easily of substituent chains with a terminal amino group particularly valuable for the constitution of the immunoadsorbants of the invention.

The monosaccharides with anchoring arms, as mentioned above constitute valuable biological reagents useful, in particular, in a form immobilised on solid supports in order to contitute immunoabsorbants.

These immunoabsorbants can be particularly used for purifying antibodies such as obtained above, or again any substance having affinity for them. They can be used also in dosage processes using this affinity.

Suitable solid supports are constituted, for example, by polysaccharides, such as celluose, agarose or crosslinked agarose (particularly that marketed under the mark SEPHAROSE by PHARMACIA), or mixed polymers containing besides the above polysaccharides polymers such as polyacrylamides (particularly those marketed under the trade marks ULTROGEL and MAGNOGEL by IBF).

The monosaccharides of the invention also enable the constitution of haptenes conjugatable to soluble supports, such as BSA (bovin serum albumine) or polylysine, intended for the preparation of polyclonal or monoclonal antibodies, Besides their use as antigenic determinants, the products of the invention are valuable as reference products for structure studies.

BRIEF DESCRIPTION OF THE DRAWINGS

Other features and advantages of the invention will appear from the examples which follow and by referring to the appended drawing, in which:

FIG. 3 shows the application of a uronic acid for making a disaccharide.

FIG. 10 to 12 show the compounds involved in exemples 16 to 19A.

Figure 1:
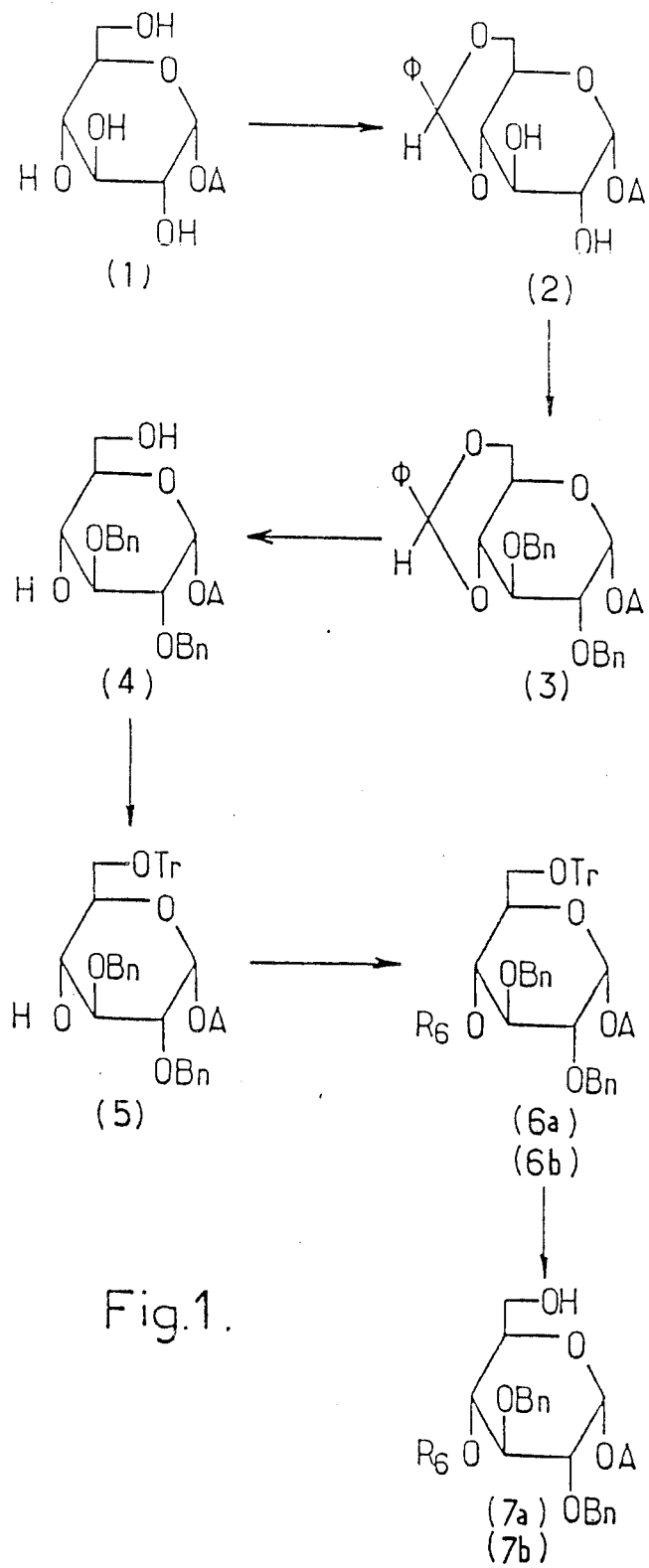
FIGS. 1 and 2 show the reactions used for preparing compounds of examples 1 to 6.
Figure 2:
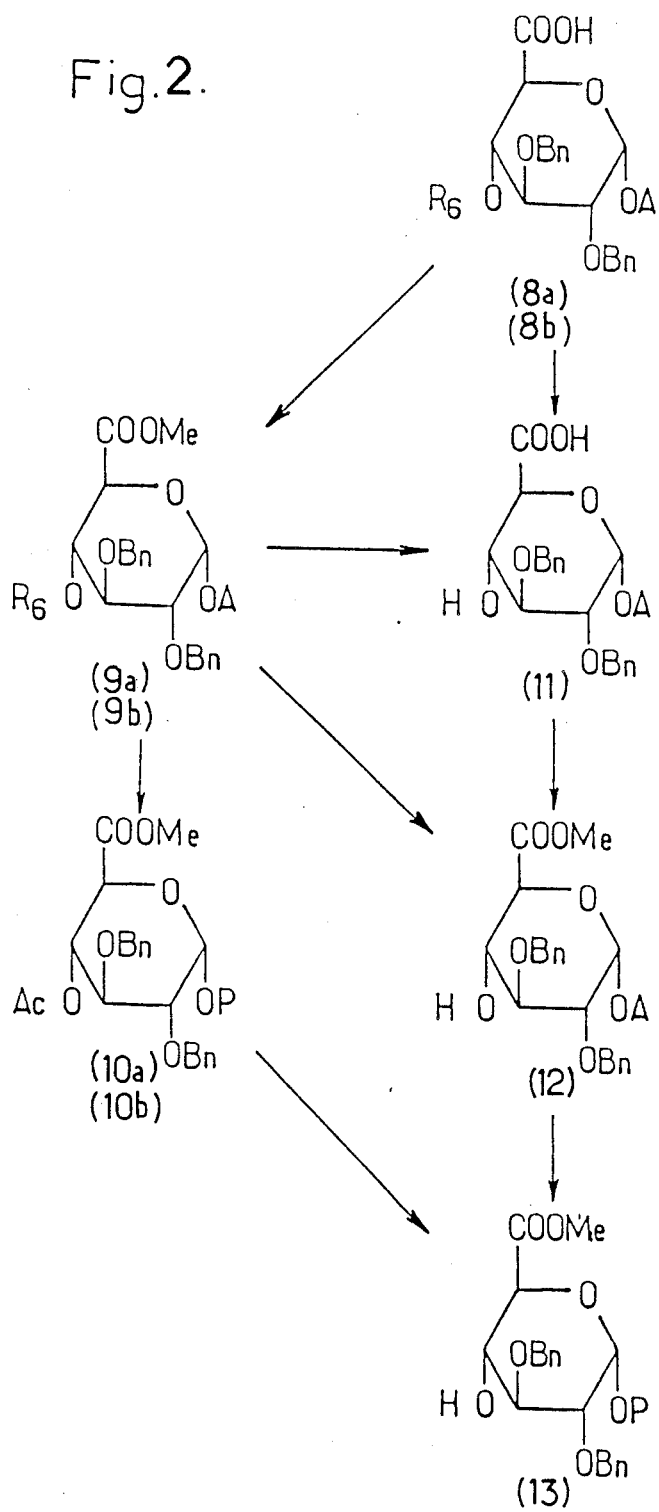

The formulae illustrating the compounds of Examples 1 to 6 are shown in FIGS. 1 and 2.

EXAMPLE 1

Preparation of (allyl-4-O-acetyl-2,3 di-O-benzyl-α-D-glucopyranoside) uronic acid (compound 8a)

This synthesis is effected from glucose, by the following steps (a) to (g):

(a) preparation of allyl α-D-glucopyranoside (compound 1)

A solution of gaseous hydrochloric acid (18 g) in allyl alcohol (600 ml) is heated to 70° C. Anhydrous glucose (300 g) is then added and it is kept at this temperature for 3 hours.

The reaction can be followed by thin layer chromatography (tlc) in the solvent methanol/chloroform (¼, v/v). The brown solution obtained after 3 hours is concentrated to dryness, under vacuum, neutralised by a concentrated ammonia solution (50 ml) then concentrated again to dryness. To the residue obtained, acetone is added (500 ml), it is brought to boiling and kept thus until fully dissolved. After cooling, the liquid is decanted. The residue is again subjected to the same treatment until the tlc analysis of the abstract shows exhaustion of the residue in derivative 1 or indeed a very high contamination of the extract by impurities. A portion of the first fraction extracted (12 g) is chromatographed on silica. Derivative 1 is recovered which can be crystallised in an acetone/ether mixture (6.5 g; mp 95°-99° C.). The remainder of the product can be purified by the same process.

(b) preparation of allyl 4,6-O-benzylidene-α-D-glucopyranoside (compound 2)

Compound 1 (37 g) is dissolved in dimethylformamide (200 ml). Dimethoxytoluene (41 g) is than added to followed by hydrated paratolunene sulphonic acid (130 mg). After 2 hours heating (water bath) under vacuum and refluxed, the reaction is terminated (t.l.c. methanol/choloroform, 2/23,v/v). The solvent was evaporated. The syrup is dissolved in methanol (the minimum), this solution is poured drop by drop into a aqueous sodium bicarbonate solution (6.3 g in 320 ml of water) The precipitate obtained was recrystallised in ethanol (21 g; m.p. 120° C.). The mother liquors yielded more of product 2. Total yield (37 g; 71.4%).

(c) preparation of allyl 2-3-di-O-benzyl-4-6-O benzylidene α-D-glucopyranoside (compound 3)

Compound 2 (45 g) was dissolved in anhydrous DMF (500 ml). Sodium hydride (28 g of a 50% dispersion in oil) was added.

After 30 minutes, the mixture was cooled to 0° C. and then, drop by drop, benzyl bromide (52 ml) was added. The reaction was followed by t.l.c. (ether/hexane, 1/1, v/v). Then methanol was added slowly (150 ml), evaporated to dryness and taken up again with chloroform. The chloroform phase was washed with water, dried over sodium sulfate. After evaporation of the solvent, the residue was crystallised in ether/hexane mixture (36.5 g: MP 83°-84° C.). This product was slightly contaminated by an impurity migrating higher in t.l.c. (ether/hexane; 1/1; v/v).

(d) preparation of allyl 2,3-di-O-benzyl-α-D-glucopyranoside—(compound 4)

To a solution of compound 3 (56 g) in methanol (1 l), was added water (450 ml) then hydrated paratoluene sulfonic acid (17 g).

After 2 hours at 80° C., the mixture was left to cool, the solvent was evaporated and the residue taken up again with chloroform (1 l). The chloroform solution was washed with water until pH neutral, then dried over sodium sulfate. This way a pale yellow syrup was obtained (48 g) which was engaged in following step (synthesis of compound 5).

(e) preparation of allyl 2,3-di-O-benzyl-6-O-trityl-α D-glucopyranoside (compound 5 ) and its 4-O-acetylated analog (compound 6a)

The derivative 4 obtained (48 g) was dissolved in pyridine (250 ml) and trityl chlorure (38.5 g) was added.

After 1 hour at 100° C., the reaction was terminated (t.l.c. ether/hexane, 1/1, v/v). The preceeding solution, acetic anhydride was added (200 ml). After one night, reaction was complete (t.l.c., ether/hexane, ¼, v/v).

It was evaporated to dryness, taken up again in chloroform (500 ml), the chloroform phase was washed with a 10% solution of acid potassium sulphate, with water and dried over sodium sulphate.

The chloroform was evaporated. In this way the compound 6 a is obtained which is used as such in a reaction for preparing a compound 7a.

(f) Preparation of allyl 4-O-acetyl-2,3-di-O-benzyl-α D-glucopyranoside (compound 7a)

The derivative 6a obtained is dissolved in chloroform (500 ml). To this solution, cooled at 10° C., is added drop by drop with stirring a solution of boron trifluoride in methanol (20%, 120 ml). The reaction is followed by t.l.c. (toluene/acetone, 10.2, v/v).

The reaction mixture is transferred to a separating funnel. The chloroform phase is washed with water (twice 100 ml) with a saturated solution of sodium carbonate, then with water until pH neutral. After drying and evaporation, the residue obtained is introduced onto a silica gel column (500 g) equilibrated in toluene. After elution of the majority of the impurities by pure toluene, the product is eluted by a toluene/acetone mixture (10/2, v/v). In this way a 48 g of the compound 7 a is obtained which is used directly in synthesis of the compound 8a. A portion of the compound 13 a was obtained pure: [α $^{20}$D=11° (chloroform). Its IR and NMR spectra, the same as the elementary analysis, confirmed the structure.

(g) Preparation of (allyl-4-)-acetyl-2,3-di-O-benzyl-αD-glucopyranoside) uronic acid (compound 8a)

A solution of the compound 7a (48 g) in acetone (800 ml) is cooled to −5° C. Then drop by drop a solution of chromium trioxide (30 g) in sulphuric acid (3.5M; 125 ml) was added. The mixture was allowed to come back to room temperature. The reaction was checked by t.l.c. (methanol/chloroform, 1/10, v/v). At the end of the reaction, the reaction mixture was poured into water (500 ml). The product was extracted with chloroform (3 times 250 ml). The chloroform phase was washed with water until pH neutral, dried over sodium sulphate and concentrated to dryness.

The syrup obtained (83 g) was used as such for the preparation of the compounds 9a.

EXAMPLE 2

Preparation of (allyl 4-O-benzoyl-2,3-di-O-benzyl-d-D-glucopyranoside) uronic acid (compound 8b) and of the corresponding methyl ester (compound 9b)

In the first step, allyl 4-O-benzoyl-2,3-di-O-benzyl-6-O-trityl-α-D-glucopyranoside (compound 6b) was firstly prepared and allyl-4-O-benzoyl-2,3-di-O-benzyl-α-D-glycopranoside (compound 7b)

(1)—preparation of the compounds 6b and 7b—The compound 6 b was obtained as described for 6a: to the pyridine solution of the compound 5, was then added benzoyl chloride (1.5 equivalents) and the reaction is followed by t.l.c. (acetate ethyl/benzene), 1/20, v/v). The excess of benzoyl chloride was destroyed by the addition of an excess of methanol. After evaporating to dryness, the residue, taken up again with chloroform, was washed with a solution of 10% $KHSO_4$, with water, dried and concentrated to dryness. The syrup obtained was engaged as such as in synthesis of compound 7b. This syrup (105 g, obtained from 30 g of compound 7) was dissolved in chloroform (300 ml). Paratoluene sulphonic acid (76 g of monohydrate in 100 ml of methanol) was added. After one night, the reaction was terminated (t.l.c., ethyl acetate/chloroform, 1/20, v/v). The chloroform phase was washed with water until pH neutral, dried and concentrated to dryness. The syrup obtained, (98 g) was chromatographed on a silica gel column (1.2 kg), eluted with chloroform (0.6 l) then with a ethyl acetate/chloroform mixture (1/20, v/v). In this way the pure derivative 7b (30 g) was obtained which was used as such in the step of preparing compound 8 b.

EXAMPLE 3

Preparation of methyl (allyl 4-O-acetyl-2,3-di-O-benzyl-α-D-glucopyranoside) uronate (compound 9a) The syrup obtained in the step of preparing the compound 8a is dissolved in ether (300 ml). An ether solution of diazomethane is then added until disappearance of compound 8a (t.l.c ether/hexane, 1/1, v/v). After acidification with acetic acid, the solvents are evaporated. The residue obtained (53 g) is dissolved in hot ethanol. The derivative 9a crystallises on cooling. After recrystallisation, this pure compound 9a is obtained (18.4 g) —mp 85°–86° C.—$[\alpha]^{20}_D = +12°$ (1.2 chloroform). This product is characterised by its IR, NMR spectra and by elementary analysis.

From the crystallisation filtrate, more of the compound 9a is obtained (7.6 g). The overall yield of 9a from the compound 2 is 38%.

EXAMPLE 4

Preparation of methyl (prop-1'-enyl 4-O-acetyl-2,3-di-O-benzyl-α-D-glucopyranoside) uronate (compound 10a)

The derivative 9a (4 g) is dissolved in a mixture of ethanol (119 ml) benzene (51 ml) and water (17 ml). Then diazabicyclo octane is added (170 mg) and it is brought to reflux. To the boiling solution Tris (triphenylphosphine)-rhodium chloride (I) (550 mg) is added. The boiling was continued for 4 hours (t.l.c., ether-hexane, 1/1, v/v).

At the end of the reaction, the solution is filtered and the solvents are removed. The residue is chromatographed on silica gel (150 g) in an ethyl acetate/chloroform mixture (1.50, v/v). Compound 10a is obtained (3.25 g; 81%) which crystallises in ethanol.

$[\alpha]^{20}_D = +12°$ (1, chloroform). MP 90° C. The structure is confirmed by elementary analysis and the NMR and IR spectra.

EXAMPLE 5

Preparation of (allyl 2,3-di-O-benzyl-αD-glucopyranoside) Uronic acid and methyl (allyl 2,3-di-O-benzyl-α-D-glucopyranoside) uronate (compounds 11 and 12)

The compounds 8b (1.9 g) is dissolved in methanol (40 ml). Then soda (5N) in a sufficient amount to have a concentration of 1M of soda is added. The reaction is followed by t.l.c. (methanol/chloroform, 1/4, v/v). When it is finished, water (100 ml) is added. It is washed with ether, acidified and the product extracted with ether. The acid ether phase is washed with water until neutral pH. The derivative 11 is not isolated. It is methylated by an ether solution of diazomethane, thus giving compound 12 (900 mg; 56%) which is then purified on a column of silica gel (ether/hexane, 1/1, v/v). $[\alpha]^{20}_D = +35.2°$ (1.3, chloroform). Its IR and NMR spectra and its elementary analysis confirm its structure.

In the same manner, the derivative 11 and hence 12 can be obtained from 9a or 9b.

EXAMPLE 6

Preparation of methyl (prop-1'-enyl 2,3-di-O-benzyl-α-D-glucopyranoside) uronate (compound 13)

1. Starting from compound 12—The derivative 12 was treated by the complex with rhodium as described for 9a. Compound 13 is obtained with a yield of 90%. It is characterised by its IR and NMR spectra. In addition, treated by acetic anhydride (1 ml for 180 mg of 9a), it gives the compound 10a.

2. From 10a or 10b—Method 1a: The derivative 10a (350 mg) is dissolved in methanol (5 ml). Sodium methoxide (0.2 ml, 2M) is added. After 1 hour at ambient temperature, the reaction was stopped by the addition of dowex resine-50-H+. After filtration, the product 13 is obtained, contaminated by a little of the product resulting from α, β-elimination. The reaction is done in the same way from 10b.

Method b: The derivative 13 may be obtained from 10a or 10b in the manner described for 12 from 9a or 9b.

EXAMPLE 6 A see FIG. 3

Application of the compound 13 to the synthesis of the disaccharide 15

To a solution of monosaccharide 13 (0.215 g; 0.5 mmole) in dichloromethane (3 ml), is added the monosaccharide 14 (0.49 g; 1 mmole) in dichloromethane (3 ml) and then 4 Å screen in powder. The mixture is cooled to 0° C., then sym-collidine (0.16 ml) and silver triflate (0.3 g) are added. After 1 hour, the mixture was diluted with dichloromethane (50 ml). The solids were drained, then the solution was washed with the 5% sodium carbonate solution, with water, then with 10% acid potassium sulphate and again with water. In this way there were obtained after evaporation 591 mg of residue. After purification on silica in a toluene/acetone mixture 30/1 (v/v), 211 mg of pure disaccharide 15 were obtained.

Figure 4:
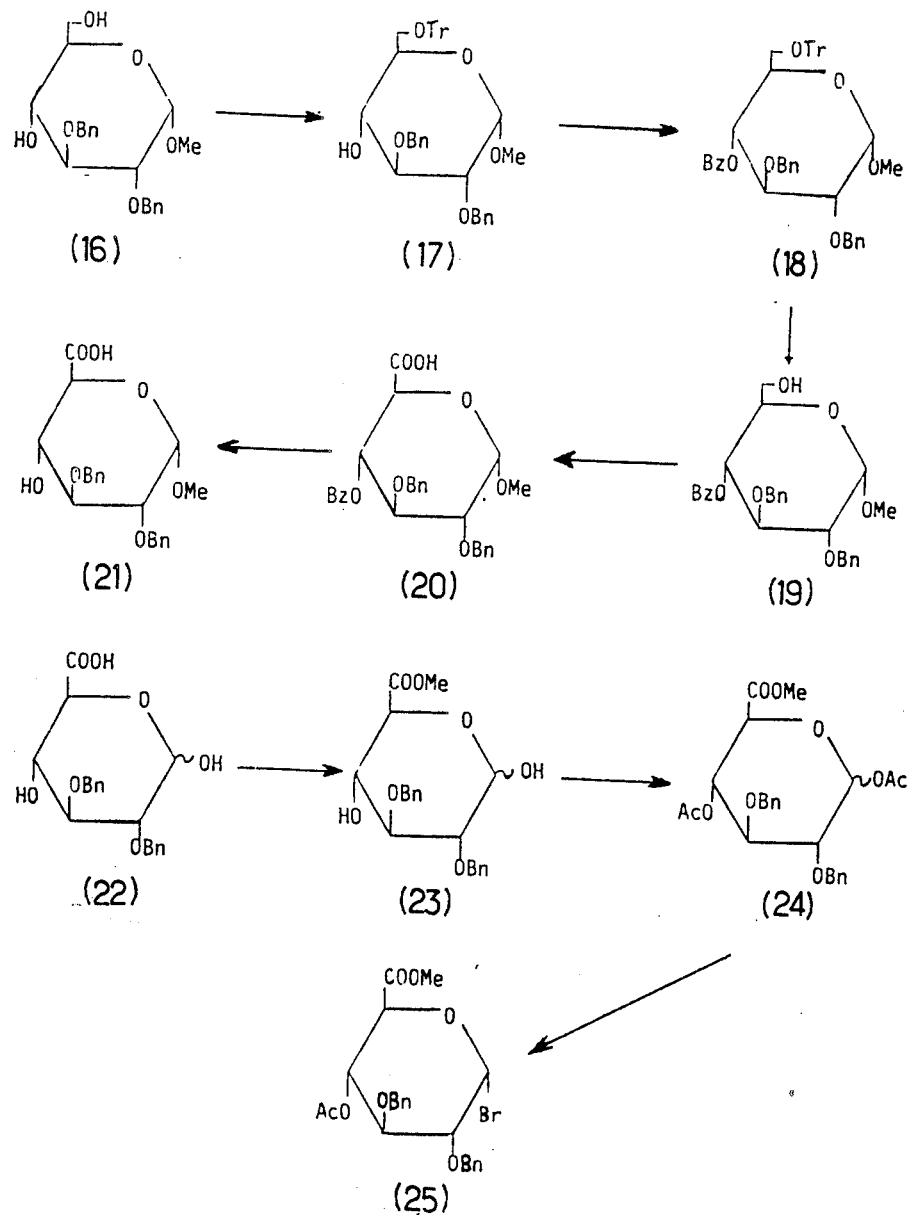
FIG. 4 shows the reactions used for preparing the compound of example 7 and FIG. 5 the use thereof for preparing a disaccharide.

EXAMPLE 7 see FIG. 4

Preparation of methyl (bromo 2,3-di-O-benzyl-4-O-acetyl-α-D-glucopyranoside) uronate (compound 25)

Synthesis of Compound 19

To a solution of 16 (32 g; 85.5 mmoles) in pyridine (250 ml), are added trityl chloride (28.6 g; 1.2 eq) and then it is heated to 80° C. The further addition of trityl chloride (4.6 g; 0.2 eq) is made after 3 hours of reaction. When the formation of 17 is complete (t.l.c. silica,; methanol/chloroform, 1/20, v/v) the solution is cooled to 0° C., then benzoyl chloride is added (15 ml; 1.5 eq). After one night 18 is formed quantitatively. Methanol (150 ml) is then added drop by drop to the reaction mixture which is then concentrated to dryness. The residue obtained is taken up again in methanol (500 ml) containing paratoluene sulphonic acid (95 g). After 2 hours of reaction, the reaction mixture is transferred to a separating funnel containing ice water (2 l). The product 19 is extracted with chloroform and then engages as such in the following step. A portion of this product was purified. An analysis of the IR spectrum confirms the structure. It is a colourless gum. $[\alpha]^{20}_D = 61°$ (chloroform).

Synthesis of Compound 23

The syrup obtained in the preceding step (95 g) was dissolved in acetone (1 l), and then to the solution cooled to 0° C., were added drop by drop, a solution of chromic oxide (52 g) in sulphuric acid 3.5M (220 ml). After 2 hours of reaction, the reaction mixture was poured into ice water (1 l). The product 20 was extracted with chloroform (5×200 ml). The chloroform phase was washed until neutral pH, dried and concentrated to dryness. To the residue obtained above, dissolved in methanol (650 ml), were added drop by drop soda dissolved in water (20 g in 50 ml), then the mixture heated to 50° C. After one night the solution obtained was concentrated partly, then poured into water (1.5 l). This aqueous phase was then washed with ether and then, after acidification with hydrochloric acid, the product 21 was extracted with ether. The ether phase was dried with sodium sulphate, then concentrated to dryness, giving a yellow mass (50 g) which contains 20.

This residue (50 g) is dissolved in a mixture of acetic acid and trifluoroacetic acid (15/1, v/v, 615 ml). To this solution stirred at 100° C., is added water (160 ml). After one night it is evaporated to dryness and the traces of acetic acid removed, then evaporation of the toluene. The residue formed in part of non-hydrolysed 21 and 22 is dissolved in ether (400 ml). To this solution is added at 0° C., an ether solution of diazomethane until complete methylation (t.l.c silica, etherhexane, 2/1, v/v). The excess of diazomethane is then destroyed by acetic acid and then the reaction mixture is concentrated to dryness.

The residue is purified on a silica gel column (200 g) diluted first by pure chloroform, then by a chloroform/ether mixture 3/1, v/v. In this way 23 is obtained (8.6 g; 22.2 mmoles, 26% by ratio to 16).

The derivative 23 is crystalline m.p. 122°-123° C. Elementary analysis and the NMR spectrum confirm its structure.

Synthesis of Compound 24

To a solution of 23 (3.9 g; 10 mmoles) in pyridine (50 ml), acetic anhydride (4 ml, 42 mmoles) was added. After 2 hours, the reaction mixture was evaporated to dryness. In this way 24 was obtained (4.62 g; 98%).

Synthesis of Compound 25

To a solution of 24 (1.4 g) in dichloromethane (30 ml) and ethyl acetate (3 ml), titanium tetrabromide (1.5 g) was added. The solution was stirred all night at room temperature. After dilution with dichloromethane, the reaction mixture is poured into ice water. The organic phase is washed with 15% bicarbonate in water, dried and concentrated. The residue is chromatographed on silica (50 g, ether/hexane, 1/1, v/v).

In this way the compound 25 (920 mg, 62%) was obtained; this is a colourless syrup $[\alpha]^{20}_D = +97.5°$ (c=1, chloroform). Elementary analysis and the NMR spectrum confirm the structure.

EXAMPLE 7A see FIG. 5 application of Compound 25 to the synthesis of disaccharide 27

This synthesis is carried out from derivatives 25 and 26. A solution of derivative 26 (432 mg, 3 mmoles) in sieve dichloromethane (10 ml) is stirred at 0° C. in the presence of a 4 Åmolecular sieve (0.5 g), drierite (1 g) and freshly prepared silver carbonate (0.42 g). After cooling to 0° C., a solution of the compound 25 (490 mg, 1 mmole) in dichloromethane (6 ml) is added drop by drop. reaction lasts two hours, the reaction mixture is then filtered. After evaporation to dryness and chromatography on silica gel the residue, (solvant: ethyl acetate/chloroform, 1,6 v/v), the derivative 27 is obtained. The structure of derivative 27 is confirmed by its elementary analysis and its NMR spectrum. Rotatory power: $[\alpha]^{20}_D = 39°$; chloroform; MP—156°-159° C.

Figure 6:
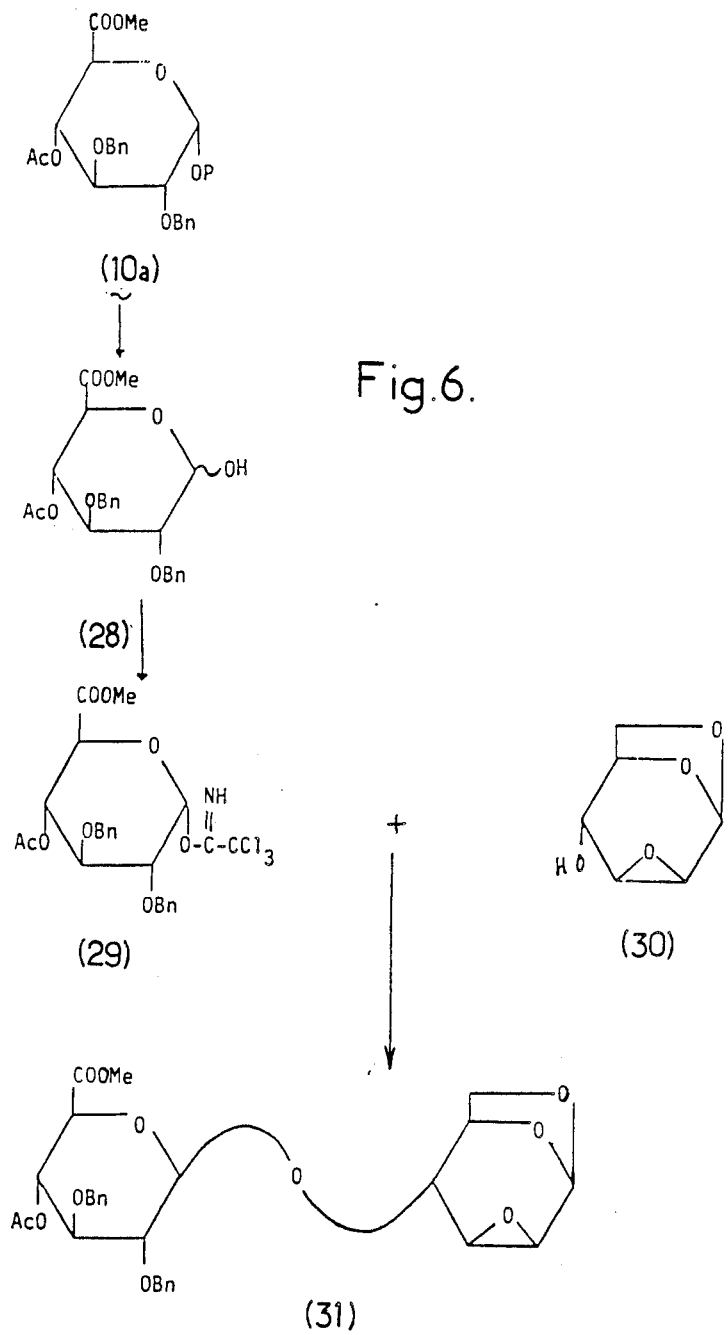
FIG. 6 shows the reactions used for preparing the compound of example 8 and the use thereof for making a disaccharide.

EXAMPLE 8 see FIG. 6

Preparation of methyl (trichloro acetimidyl 2,3-di-O-benzyl-4-O-acetyl) uronate (compound 29)

Synthesis of Compound 10a

Compound 10a (11,4 g) is dissolved in an acetone/water mixture (5/1; v/v; 350 ml). To this solution mercuric oxide (13.5 g) is added, then, drop by drop, a solution of mercuric chloride in the mixture acetone/water (17 g in 116 ml). After 5 minutes, the mixture is filtered and then the solvents are evaporated. The residue, taken up again with chloroform (300 ml) is washed with a saturated solution of potassium iodide and then with water.

After drying and evaporation to dryness, the residue is purified on a silica gel column (200 g hexane/ethyl acetate, 1/1, v/v). In this way 28 is obtained (6 g; 57,5%). It is a solid, m.p. 104°-106° C. $(\alpha)^{20}_D$: −4,5 (1,2 chloroform), The NMR spectrum and elementary analysis confirm the structure.

Synthesis of Compound 29

To a solution of compound 10a (3,46 g; 8 mmoles), of trichloro-acetonitrile (8 ml; 10 eq) in dichloromethane (80 ml), sodium hydride (135 mg) is added. the development of the reaction is followed by t.l.c. (chloroform-/ethyl acetate; 1/1; v/v). After filtration, the solution is concentrated to dryness, then the residue is dried by evaporation of benzene before being engaged in the reaction with 29.

EXAMPLE 8A
see FIG. 6

Application of compound 29 to the synthesis of disaccharide 31

Synthesis of Disaccharide 31

The product- 29 obtained above (from 8 mmoles of 28) is dissolved in dichloromethane (40 ml) containing the derivative 30 (1,1 g; 7,6 mmoles). To this solution is added drop by drop, a solution of boron trifluoetherate in dichloromethane (0,6 eq). The development of the reaction is checked by t.l.c. (chloroform/ethyl acetate 6/1 v/v). Solid sodium bicarbonate is added until neutralisation, then the dichloromethane phase is washed with water until pH neutral. After drying and evaporation of the solvents, the syrup obtained is chromatographed on silica gel (200 g, chloroform/ethyl acetate, 8/1, v/v).

In this way the compound 31 is obtained (1.56 g). The other monomer ($\alpha$-D-glucuronosyl) is also obtained in less amount (250 mg.). 29 is in all aspects similar to product 31 described in patent application FR 82 00621 of Applicant.

Figure 7:
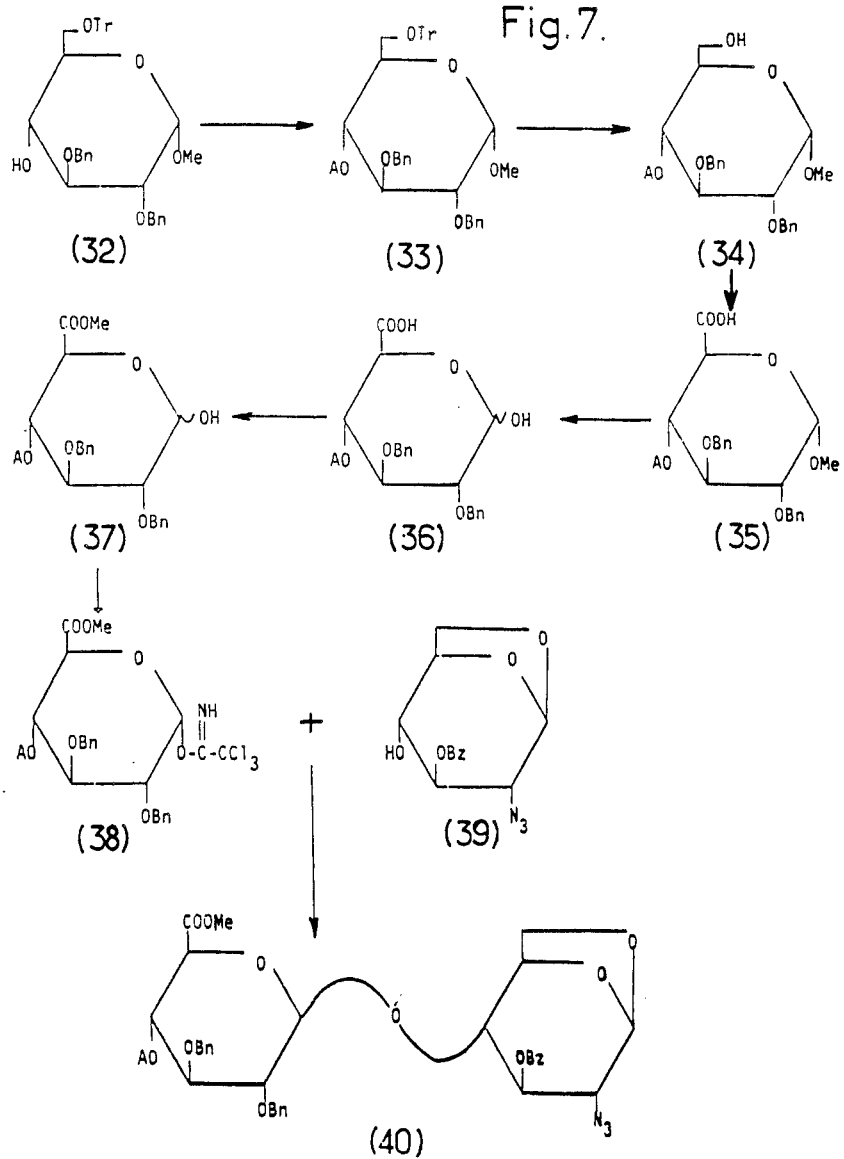
FIG. 7 shows the reactions used for preparing the compound of example 9 and the use thereof for making a disaccharide.

EXAMPLE 9
see FIG. 7

Preparation of methyl (trichloroacetimidyl-2,3-di-O-benzyl-4-O-allyl-$\alpha$-D-glucopyranoside) uronate (compound 38)

Synthesis of Derivative 37

Compound 32 was allylated conventionally (sodium hydride, allyl bromide in dimethylformamide) to give the compound 33. The latter is then subjected to a series of reactions identical with those described above for compound 18. (detrilylation, oxidation, hydrolysis, methylation). At this stage the product is purified on a silica gel column (200 g; chloroform/ethyl acetate: 10/1; v/v). The compound 37 is obtained in the form of a syrup $[\alpha]^{20}_D + 23,5°$ (1 chloroform). The IR spectrum and the elementary analysis confirm the structure.

Synthesis of 38

The compound 37, treated (as described for 17), by trichloro acetonitrile in the presence of sodium hydride results in the imidate 38 which is used in the synthesis of 40.

EXAMPLE 9A
see also FIG. 7

Application of compound 38 to preparation of disaccharide 40

Synthesis of Disaccharide 40

To a solution of 38 (615 mg; 1.1 mmole) and of 39 (300 mg; 1 mmole) in dichloromethane (5 ml), was added at 20° C., a solution of boron trifluoro-etherate (1 mmole) in dichloromethane (10 ml). The reaction is followed by t.l.c. (acetone/toluene; 1/10:v/v). The reaction mixture is diluted with dichloromethane and then neutralised by sodium bicarbonate (500 mg). The solution obtained is washed with a saturated solution of sodium chloride, dried, then concentrated to dryness. The residue was chromatographed on a silica gel column (50 g.; toluene/isopropyl ether; 4/1; v/v). In this way 40 is obtained (147 mg; $[\alpha]^{20}_D + 11°$—chloroform-) and the isomere, (162 mg: $[\alpha]^{20}_D + 48°$—1, chloroform-). Elementary analysis and study of the NMR spectra confirm the structures of the products.

Figure 8:
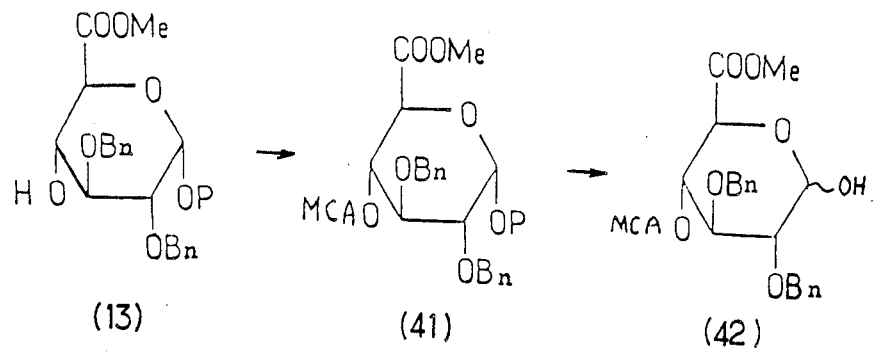
FIG. 8 shows the reactions used for preparing the compounds of example 10 to 12 A.
Figure 8:
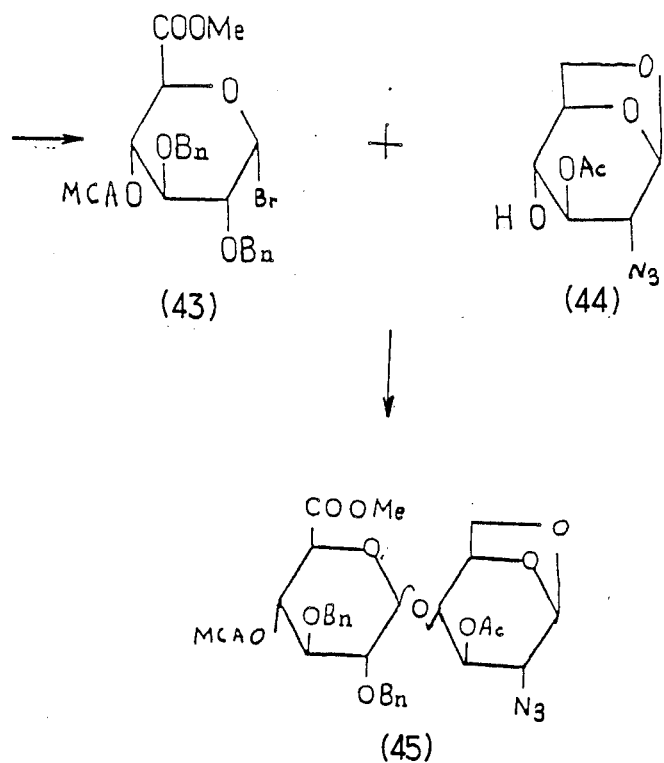

The formulae of Examples 10 to 12A are shown in FIG. 8.

EXAMPLE 10

Preparation of methyl (propy-1-ethyl 1,2,3-di-O-benzyl-4-O-chloroacetyl-$\alpha$-D-glucopyranoside) uronate (compound 41)

This synthesis was carried out from compound 13 of example 6 or methyl (prop-1'-ethyl-2,3-di-O-benzyl-$\alpha$-D-glucopyranoside) uronate by proceeding as follows:

2.8 g of compound 13 is dissolved in 30 ml pyridine (6,56 mmoles). After cooling to 0° C. 10 ml of a solution of 2 ml chloroacetyl chloride in 20 ml dichloromethane is added. After 30 minutes, it is evaporated to dryness, the residue is taken up again in 200 ml of chloroform, it is washed with a 10% solution of KHSO$_4$, then with water, dried and concentrated. The syrup obtained is chromatographed on silica gel (200 g; eluant AcOEt/hexane; 1/3; v/v). In this way 2.7 g of pure compound 41 obtained in the form of a syrup (yield 80%); $[\alpha]^{20}_D = +2°$ (c=1.5; chloroform). Elementary analysis and the NMR spectrum confirm the expected structure.

EXAMPLE 11

Preparation of methyl (2,3-di-O-benzyl-4-O-chloroacetyl-D-glucopyranose) uronate (compound 42)

2.7 g (5.3 mmoles) of the derivative 41 are dissolved in 80 ml of an acetone/water mixture (5/1; v/v). Mercuric oxide (3.1 g) is added followed by a solution of mercuric chloride (3.9 g) in acetone (27 ml). After 5 minutes, the salts were removed by filtration. After concentration to dryness, the residue was taken up again by chloroform. The chloroform phase is washed with a solution of 10% KI then with water. After evaporation, the product is crystallised in an ethyl acetate/hexane mixture. 2 of a solid of mp 105°–107° C. is obtained; $[\alpha]^{20}_D = -4.7°$ (eq, 1; chloroform). Elementary analysis and the NMR study confirm the structure (yield 80%).

EXAMPLE 10

Preparation of methyl (1-bromo-2,3-di-O-benzyl-4-O-chloroacetyl-$\alpha$-D-glucopyranosyl) uronate (compound 43) 2 g (4.30 mmoles) of compound 42 is dissolved in 50 ml of dichloromethane. 4.8 ml (34.4 mmoles) of sym-collidine at 0° C. is added followed by bromomethylene dimethyl ammonium bromide (17 mmoles) prepared according to HEPBURN D. R. and HUDSON H. R. J. Chem. Soc. Perkin I (1976) 754–757. After 4 hours of reaction, the mixture is diluted with 100 ml of dichloromethane, then poured into ice water. After washing with ice water, the solvent is evaporated. After chromotography on silica gel, (20 g); eluant hexane/ethyl acetate, 2/1; v/v), 2.06 g of compound 43 is obtained in the form of a syrup (yield 90%). $[\alpha]^{20}_D = +82.5°$ (c=1.5; chloroform). Elementary analysis and the NMR study confirm the structure.

EXAMPLE 12A

Application of the compound 43 to synthesis of the disaccharide 45 or (3,O-acetyl-1,6-anhydro-2-azido-4-O-[(2,3-di-O-benzyl-4-O-chloroacetyl-β-D-glucopyranosyl) methyl uronate]β-D-glucopyranose To a solution of 870 mg (3.8 mmoles) of compound 44 in dichloromethane, is added 1 g of drierite (0.5 g of molecular sieves 4 Å, in powder form and 0.525 g of freshly prepared silver carbonate. After 2 hours stirring, compound 43 is added drop by drop at 0° C., 670 mg (1.3 mmoles). After 6 days, the solids were removed by filtration. The syrup obtained after concentration is chromatographed on silica gel (50 g; eluant: chloroform/ethyl acetate; 4/1, v/v). The disaccharide 1 is obtained in the form of a foam (421 mg: 50%).

$[\alpha]^{20}_D = -17°$ (c=1; chloroform). Elementary analysis confirms the structure. NMR study confirms the configuration of the interglycosidic bond.

Figure 9:
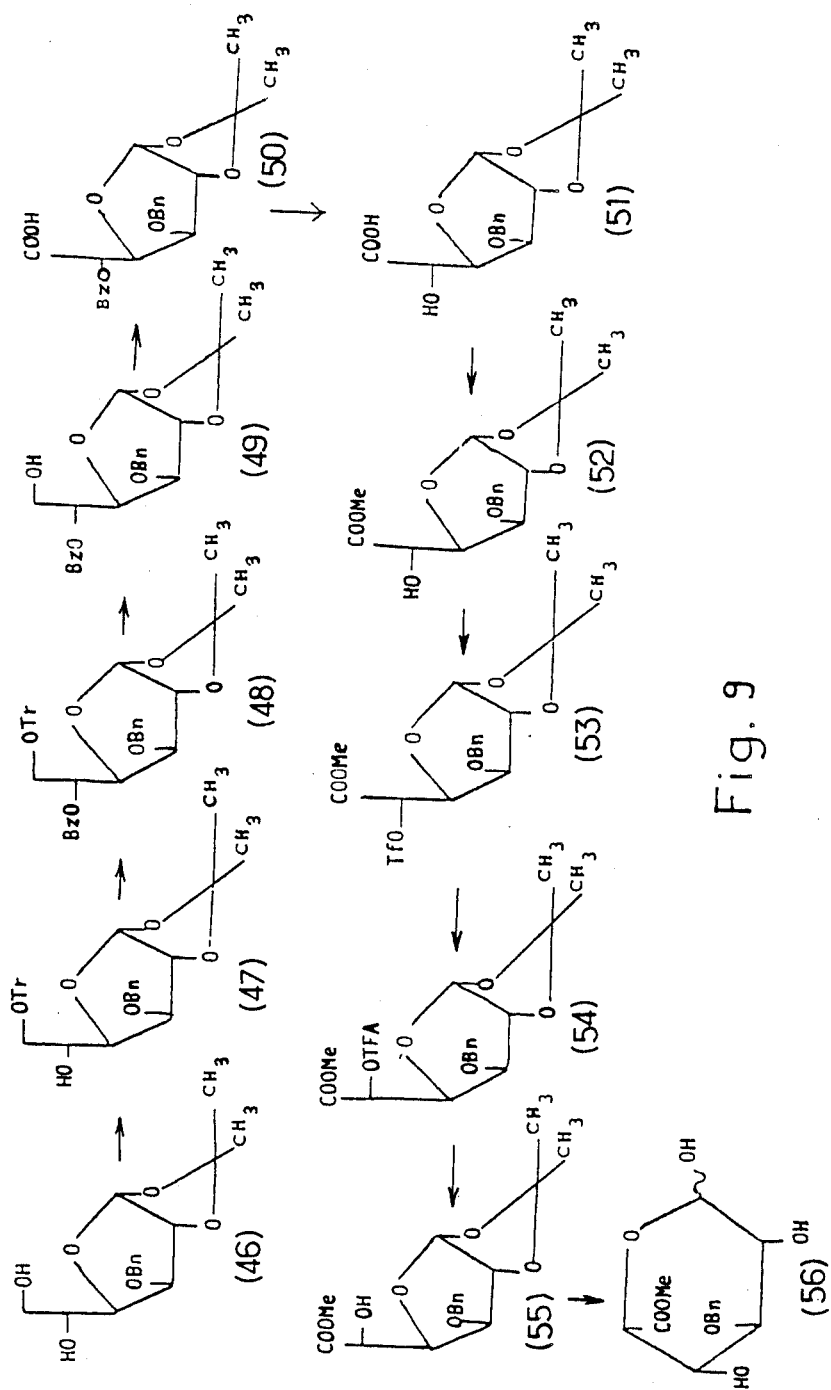
FIG. 9 shows the reaction used for making the L-iduronic acid derivative in example 13.

EXAMPLE 13 see FIG. 9

Preparation of methyl (3-O-benzyl-α-L-glucopyranoside) iduronate (compound 56) of formula

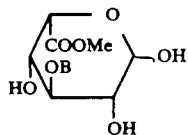

This synthesis is carried out from compound 46 by the following steps:
(1) introduction of a benzoyl group at the 5 position,
(2) methylation of the carboxyl function at the 6 position,
(3) isomerisation of the OH group at the 5 position,
(4) formation of the pyran ring.

(1) benzoylation reaction 63 g of 3-O-benzyl-1,2-O-isopropylidiene-α-D-glucofuranoside (compound 46) are dissolved in 500 ml of anhydrous pyridine. 85 g of trityl chloride is added and it is heated to 80° C. for one hour. IN this way the compound 47 is obtained.

Rotatory power: $[\alpha]^{20}_D = -34.7°$, chloroform.

The structure of this compound has been confirmed by its IR and NMR spectra, its elementary analysis is correct.

The mixture is then cooled to 0° C. and 45 ml of benzoyl chloride added. After one night, the excess of reagents are destroyed by the addition of 300 ml of methanol. The mixture obtained, evaporated to dryness, is taken up again by chloroform. The chloroform phase is washed with water, dried over sodium sulphate and concentrated. In this way the compound 48 is obtained.

The syrup obtained is dissolved in 400 ml of chloroform. After addition of 100 ml of a 5M paratoluene-sulphonic acid solution in methanol, the solution is left at 4° C. over night. After washing the organic phase with water, 215 g of a mixture is obtained. The compound is obtained by chromatography of this mixture on silica gel in the solvent ether-hexane 2/1 (v/v). In this way 36 g of the compound 49 is obtained.

Rotatory power: $[\alpha]^{20}_D = 65.3°$, chloroform.

The structure of the compound 49 was confirmed by IR and NMR spectra.

(2) methylation of the carboxyl function at the 6 position

The compound 49 (1.88 g) is dissolved in acetone (20 ml). Drop by drop at −50° C., 3.5 ml of a CrO₃ (13 g) solution in 3.5M H₂SO₄ (29 ml) is added. The temperature is allowed to rise again and it is left for one hour under these conditions. The reaction mixture is then poured onto ice and the product is extracted with chloroform. After washing with water and drying, it was evaporated to dryness. The compound 50 is obtained.

The mixture obtained is dissolved in methanol (20 ml), then 10 ml of 1 N soda is added and it is left to stand over night at room temperature. The reaction mixture is then passed through a column of Dowex 50 resin (25 ml) in the H⁺ form previously rinsed with methanol. The product is obtained by concentration of the eluate. In this way the compound 51 is obtained.

This compound is dissolved in ether and methylated conventionally with diazomethane. After evaporation, the compound 52 is obtained (1.08 g; 70.4%). Rotatory power: $[\alpha]^{20}_D = -27°$, chloroform.

Elementary analysis found that it was correct for compound 52. Its structure is in addition confirmed by IR and NMR spectra.

(3) isomerisation of the —OH group at the 5 position

To a triflic anhydride solution (0;8 ml) in dichloromethane (16 ml), cooled to −20° C., is added drop by drop a solution of pyridine (0.8 ml) in dichloromethane (8 ml). After one hour at −50° C., the reaction mixture is poured into mixture of water and ice (8 ml) containing 160 mg of sodium bicarbonate. It is stirred until separation of the two organic and aqueous phases. The organic phase is washed with 3% HCl, H₂O, saturated NaCl, dried and concentrated. In this way the compound 53 is obtained.

The syrup is taken up again with DMF (10 ml). Sodium trifluoroacetate (1.6 g) is added and it is heated to 80° C. for 3 hours. In this way this compound 54 is obtained. After evaporation, taking up again with dichloromethane, washing with water and drying, the residue is taken up again with methanol then the solvent is evaporated after one hour. After chromatography on a column in the solvent ether-hexane 2/1, the compound 55 is obtained (450 mg: 56.2%).

Rotatory power: $[\alpha]^{20}_D = -33°$ chloroform.

The structure of the compound 55 is confirmed by its IR and NMR spectra. Elementary analysis found is correct.

(4) formation of the pyranic ring

This synthesis is carried out from compound 55. Compound 55 (200 mg) is dissolved in a trifluoroacetic-/acid/water 9/1 mixture). After 15 minutes, the solvents are evaporated. The residue is crystallised in ethyl acetate/hexane. In this way 110 mg of compound 56 is obtained.

The characteristics of this derivative are as follows:
IR spectrum: in CHCl$_3$, $\gamma$ in cm$^{-1}$: 3450(OH), 3080, 3060, 3030 (CH$_2$:benzyl) and 1740 (COOCH$_3$).

NMR spectrum: $\delta$ in ppm with a respect to TMS: 3.75 (s, 3 H$^+$, COOMe) 4.98 (1 H$^+$), 7.30 (d, 5 H$^+$, C$_6$H$_5$).
rotatory power: $[\alpha]^{20}{}_D = +13°$, methanol.
elementary analysis for

|   | calculated | found |
|---|---|---|
|   | C$_{14}$H$_{18}$O$_7$ | |
| C | 56.37 | 56.17 |
| H | 6.08 | 5.85 |
| M.P. | 125–126° C. | |

EXAMPLE 14 see FIG. 10

Preparation of compounds 57 and 58 or 1,2,4-tri-O-acetyl-3-O-benzyl-$\alpha$, $\beta$-L-methyl idopyranuronate A solution of compound 56 (3 g) prepared according to patent application FR No. 82 00621, in the name of Applicant), in a mixture of anhydrous pyridine (20 ml) and acetic anhydride (10 ml) is stirred at 0° C., protected from moisture, for 5 h. The reaction mixture is evaporated to dryness, evaporated with toluene (4×20 ml), and dried under vacuum. The residue is chromatographed on a silica gel column (150 g). Elution by the mixture toluene: ethyl acetate (4:1 v/v) gives, in order of elution:

a head fraction composed of furane derivatives, compound 58 ($\alpha$anomer), syrup, (170 mg, 4%), $[\alpha]_D = -43°$; (c: 1, chloroform), N.M.R. (CDCl$_3$): $\delta$: 6.23 (s, 1 H, H-1).

compound 57 ($\beta$anomer), crystallising in an etherhexane mixture, (2.688 g, 63%) M.P.: 112°–113° C., $[\alpha]_D = +9°$ (c,: 1, chloroform) N.M.R. (CDCl$_3$):$\delta$:6.08 (d, 1 H, H-1, J$_{1,2}$:1.5 Hz).

The $\alpha$ and $\beta$ anomers 57 and 58 are not prepared when following the succession of syntheses described. Their mixture is used directly in the form of a syrup for subsequent reactions.

EXAMPLE 15 see also FIG. 10

Preparation of 2,4-di-O-acetyl-3-o-benzyl-$\beta$-L-methyl idopyranuronyl bromide (compound 59)

A mixture of acetates 57 and 58 (212 mg, 0.5 mM) is dissolved in anhydrous dichloromethane (5 ml) and anhydrous ethyl acetate (0.5 ml). Titanium tetrabromide (250 mg, 0.7 mM) is added in one batch, and the reaction mixture is stirred 24 h at room temperature protected from moisture. After cooling to 0° C. and dilution with dichloromethane, the organic phase is washed with ice water (3 times), dried (sodium sulphate), filtered and evaporated to give 59 in the form of a slightly coloured syrup (217 mg, 96%), N.M.R. (CDCl$_3$):$\delta$:6.41 (s, 1 H, H-1). This very unstable compound is immediately applied in the following reactions.

The formulae of the compounds of Examples 16 to 19A are shown in FIGS. 10 and 11.

EXAMPLE 16

Preparation of 4-O-acetyl-3-O-benzyl-1,2-O-methoxyethylidene-$\beta$-L-methyl idopyranuronate (compound 60)

A solution of the bromide 59 (freshly prepared from 0.425 g, 1 mM of a mixture of acetates 57 and 58 ) in anhydrous dichloromethane (10 ml) is stirred at room temperature under a dry argon atmosphere. Sym-collidine (0.66 ml, 5 mM) and anhydrous methanol (0.40 ml, 10 mM) were successively added, and the reaction mixture stirred 20 h under these conditions. After dilution with dichloromethane (50 ml), the organic phase is washed with a saturated aqueous solution of sodium hydrogencarbonate, with water, dried (sodium sulphate), filtered and evaporated. The residue is chromatographed on a silica gel column (20 g). Elution by the mixture hexane:ethyl acetate (3:2 v/v, containing 0.5% of triethylamine) gives 60 in the form of a pure syrup (302 mg, 76% from 57 and 58), $[\alpha]_D = -21°$ (c: 1, chloroform), N.M.R. (CDCl$_3$):$\delta$:5.52 (d, 1 H, H-1, J$_{1,2}$:3 Hz).

EXAMPLE 17

Preparation of 4-O-acetyl-3-O-benzyl-1-1,2-O-tertbutoxyethylidene-$\alpha$-L-methyl idopyranuronate (compound 61)

A solution of 59 bromide (freshly prepared from 2.122 g, 5 mM, of an acetate mixture 57 and 58 in anhydrous dichloromethane (20 ml) is stirred at room temperature under a dry argon atmosphere. Sym-collidine (2.65 ml, 20 mM) and anhydrous tert-butanol (3 ml, 30 mM) are successively added, and the reaction mixture is stirred 15 h under these conditions. After identical treatment with that described for the compound 60, the residue is chromatographed on a silica gel column (120 g). Elution by the mixture hexane:ethyl acetate (2:1, v/v, containing 0.5% of triethylamine) gives 61 in the form of a pure syrup (1.542 g, 70%) from 57 and 58, $[\alpha]_D = -23°$ (c:1, chloroform), N.M.R. (CDCl$_3$) :$\delta$:5.48 (d, 1 H, H-1, J$_{1,2}$:2.5 Hz.).

EXAMPLE 18

Preparation of 3-O-benzyl-1,2-butoxyethylidene-L-methyl idopyranuronate compound 62)

A solution of the 61 orthoester (484 mg, 1.1 mM) in anhydrous methanol (15 ml) is cooled to −20° C. with stirring and in a dry argon atmosphere. Anhydrous potassium carbonate (60 mg) is added, and the reaction mixture is stirred 5 h under these conditions. The solids were drained, the filtrate was evaporated and the residue was taken up again in chloroform (50 ml). The organic phase is washed with ice water (3 times) dried (sodium sulphate), filtered and evaporated. The residue is chromatographed rapidly on a silica gel column (25 g). Elution by the mixture hexane:ethyl acetate (2:1, v/v, containing 0.5% of triethylamine), gives, in order of elution:

the unsaturated compound 64 (31 mg, 7%) syrup, $[\alpha]_D = +103°$ (c:1, chloroform), N.M.R. (CDCl$_3$) :$\delta$:6.27 (d.ded., 1 H, H-4, J$_{3,4}$:5 Hz, J$_{2,4}$:1 H$_z$), 5.67 (d, 1 H, H-1, J$_{1,2}$:4 Hz).

a principal fraction (271 mg, 62%) which is crystallised in a ether-hexane mixture to give 62 (123 mg, 28%), M.P.:68°-69° C.;$[\alpha]_D = -19°$ (c:1, chloroform), N.M.R. (CDCl$_3$:$\delta$:5.41 (d, 1 H, H-1, $J_{1,2}$:2 Hz), 2.85 (d, 1 H, CH-4, J:12 Hz, exchanged with D$_2$O).

In the course of chromatography on silica, and during crystallisation tests of 62, a novel compound of Rf slightly higher than that of 13 appears. Chromatography on silica gel of the mother liquors from crystallisation of 62 enables the isolation of some pure fractions of this novel compound 65 (41 mg, 11%), syrup, $[\alpha]_D = +21°$ (c:1, chloroform, N.M.R. (CDC$^1_3$) :$\delta$:5.83 (d, 1 , H-1, $J_{1,2}$:4.5 Hz).

Within the scope of the succession of synthesis envisaged according to the invention, in order to avoid formation of 65, the crude syrup of 62 is not chromatographed, but used immediately for the following reaction.

EXAMPLE 19

3-O-benzyl-4-O-chloroacetyl-1,.2-O-tert-butoxyethylidene-δ-L-methyl idopyranuronate (compound 53)

A solution of the orthoester 62 (220 mg), 0.5 mM) in anhydrous methanol (10 ml) is cooled to 31 20° C. with stirring and dry argon atmosphere. Anhydrous potassium carbonate (40 mg) is added and the reaction mixture is stirred for 5 h under these conditions. The solids are drained, the filtrate is evaporated and the residue is taken up again in chloroform (50 ml). The organic phase is washed rapidly with ice water (3 times), dried (sodium sulphate), filtered and evaporated. The residue is immediately dissolved in the anhydrous pyridine (4 ml) and anhydrous dichloromethane (2 ml). After cooling to −20° C. under dry argon atmosphere, a solution of chloroacetyle chloride (0.1 ml, 1.25 mM, freshly distilled) in anhydrous dichloromethane (1 ml) is added drop by drop. The reaction mixture is stirred under these conditions for 30 minutes, then poured into a water-ice mixture (100 ml). After stirring for 15 min, the mixture is extracted with chloroform (3×20 ml). The organic phases are washed with ice water, with an aqueous 2% solution of sodium hydrogencarbonate, and with water, dried (sodium sulphate), filtered and evaporated. The residue is chromatographed rapidly on a silica gel column (12 g). Elution by the mixture hexane:ethyl acetate (5:2, v/v, containing 0.2% of triethylamine) gave, in order of elution:

the unsaturated compound 64 (15 mg, 8%), the orthoester 63 syrup (145 mg, 61% from 12), $[\alpha]_D = +19°$ (c:1, chloroform), N.M.R. (CDCl$_3$):$\delta$: 5.45 (3, 1 H, H-1, $J_{1,2}$:2.5 Hz). 5.24 (d,de d, 1 H , H-4, $J_{3,4}$:2.5 Hz, $J_{4,5}$:1.5 Hz), 4.00 (s, 2 H, Cl—C$\underline{H}_2$—COO—)

EXAMPLE 19A see FIG. 12

Application of the compound 63 to the synthesis of the disaccharide 67

Compound: Methyl 6-O-benzoyl-3-O-benzyl-2-benzyloxycarbonylamino-2-desozy-4-O-(2.4-di-O-acetyl-3-O-glucopyranoside A solution of the orthoester 63 (80 mg, 0.2 mM) and alcohol 66 (52 mg, 0.1 mM) in anhydrous chlorobenzene (8 ml) is heated to 140° C. with stirring and a slight flow of dry argon. After slow distillation of 6 ml of solvent, a solution of 2,6 dimethylpyridinium perchlorate (0.002 mM freshly prepared according to N. K. KOCHETKOV, A. F. BOCHKOV, T. A. SOKOLOVSKAIA and V. J. SNIATKOVA, Carbonhdr. Res., 16 (1971) 17-27, in chlorobenzene (2 ml) is added drop by drop in 15 min. with simultaneous distillation of solvent (2 ml). The reaction mixture is then stirred for 1 h, under these conditions, with the addition of fresh solvent (10 ml) and simultaneous distillation so that the reaction volume remains constant and equal to 2 ml. After cooling and dilution with chloroform, the organic phase is washed with a saturated solution of sodium hydrogencarbonate, with water, dried (sodium sulphate) filtered and evaporated. The residue is chromatographed on a silica gel column (15 g). Elution by the mixture hexane:ethyl acetate (4:3, v/v) gives, in order or elution:

the starting material 66 (20 mg, 38%), a homogenous fraction in thin layer chromatography (54 mg). The N.M.R. spectrum of this fraction shows the presence of several O-methyl signals ($\delta$:3.35-3,50) due to the methyl glycosides arising from the rearrangement of the orthoester 53. This fraction is crystallised in an ethanol-water mixture, and recrystallised in an ethyl acetate-hexane mixture to give 67 (44 mg, 50%), M.P.: 120°-121° C., $[\alpha]_D = +17°$ (c: 1, chloroform), N.M.R. (CDCl$_3$): in arrangement with the expected structure.

Figure 13:
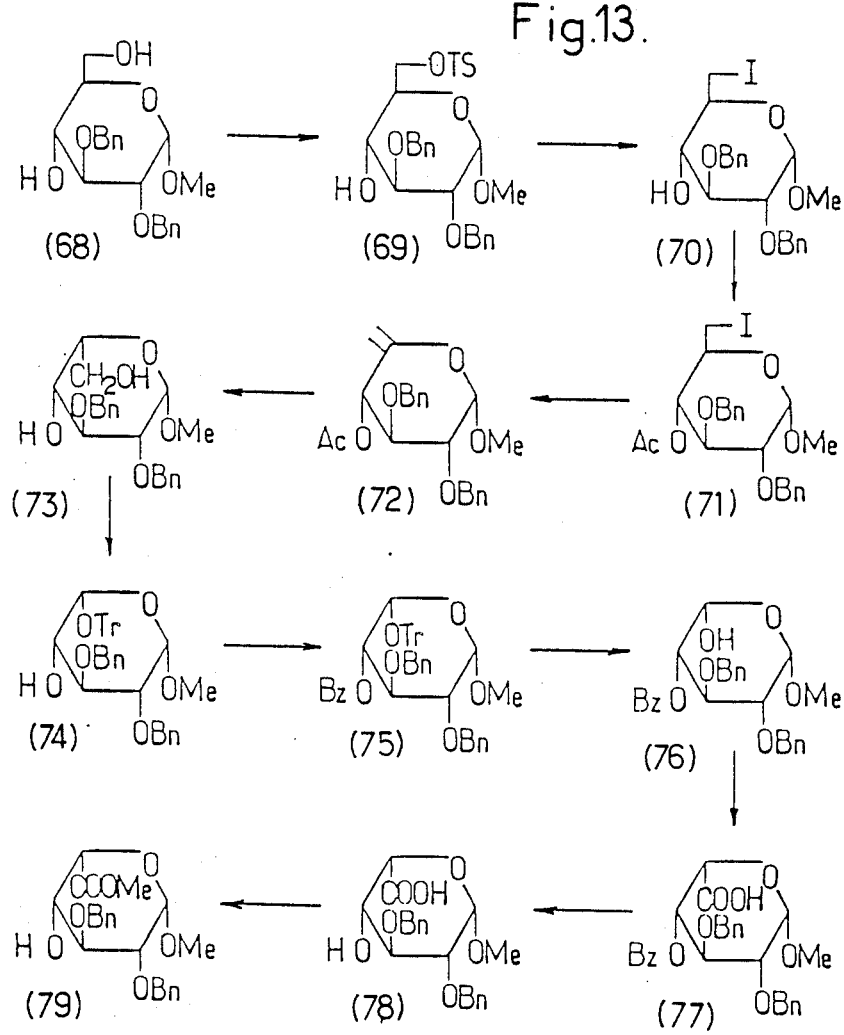
FIG. 13 shows the reactions used for preparing the compounds in example 20 and FIG. 14 use thereof for obtaining a disaccharide.
Figure 14:
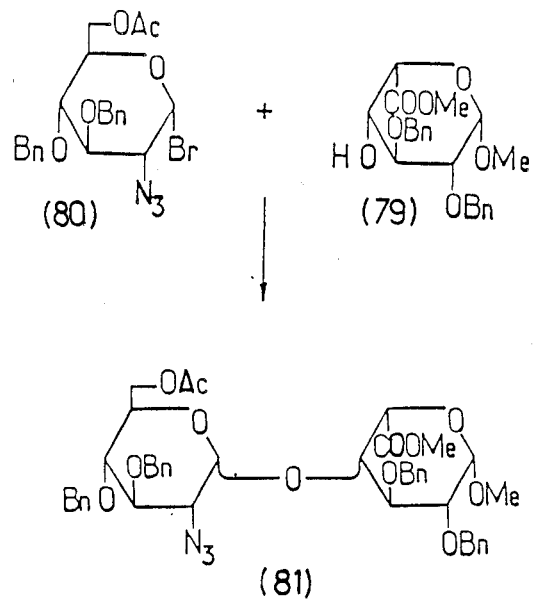

EXAMPLE 20 see FIG. 13

Preparation of methyl (methyl-2,3-di-O-benzyl-δ-L-glucopyranoside) iduronate (compound 79)

This synthesis is carried out by the following steps 1 to 7.

Step 1: synthesis of the monosaccharide 69

This monosaccharide is prepared from compound 68 obtained by the technique of N. L. Holder and B. Fraser-Reid, Canadian Journal of Chemistry, 51 (1973) page 3357. To a solution of compound 68 (1 g, 12.67 mM) in dichloromethane (20 ml), there is added tosyl chloride (0.55 g), then dimethylaminopyridine (16 mg) and finally, triethylamine (0.7 ml ). After stirring under a flow of nitrogen protected from moisture, for about 14 hours, the reaction is stopped by the addition of ice and water. After dilution of the rareaction mixture with dichloromethane (50 ml), the dichloromethane phase is washed with 2M hydrochloric acid, then a saturated solution of sodium bicarbonate, and finally with water until pH neutral. After drying and evaporation, a residue is obtained, namely the derivative 69 (1.4 g, 97%) which is engaged as such in the synthesis of the derivative 70.

Step 2: synthesis of the derivatives 70

The monosaccharide 69 (31.8 g) and sodium iodide (39 g) are dissolved in acetonitrile (250 ml), then the solution is brought to reflux for 3 hours. After cooling the reaction mixture, the white precipitate form is filtered. The filtrate is concentrated, the residue is taken up again with chloroform, then the chloroform phase is washed with water until pH neutral, dried over sodium sulphate and concentrated to dryness. A syrup is obtained which is chromatographed on a silica gel column (200 g, ether-hexane, 1/1, v/v). In this way the iodised derivative is obtained (24.7 g, 71.5%). $[\alpha]^D{}_{20}=24°$ (1, chloroform), The infrared spectrum, the NMR spectrum and elementary analysis confirm the structure of 70.

Step 3: synthesis of the derivative 71

To a solution of the derivative 70 in anhydrous pyridine (200 ml), acetic anhydride (43 ml) is added. After about 14 hours with stirring, the reaction is terminated. The reaction mixture is concentrated to dryness, then the residue is purified on a silica gel column under pressure, in an ethyl acetate-hexane solvent (1/6, v/v). The pure fractions are grouped together. In this way the product 71 is obtained (16.4 g, 70%). This product is in the form of a syrup $[\alpha]^D{}_{20}=+4.5°$ (1.3, chloroform). Elementary analysis and analysis of the infrared spectrum confirm the structure.

Step 4: synthesis of 72

To a solution of derivative 71 (4 g) in pyridine (100 ml), cooled to 0° C., silver fluoride is added (AgF, 6.9 g). After two hours and a half, the reaction mixture is poured into a mixture containing chloroform and ether (¼, v/v, 1 l). The suspension obtained is passed through a pleated filter. The filtrate is concentrated to dryness, then the residue is taken up again in chloroform (500 ml). The chloroform phase is washed with acid potassium sulphate in 10% solution in water, then with water until pH neutral. After drying over sodium sulphate and concentration to dryness, a residue is obtained (2.7 g) which is chromatographed on a silica column (200 g), (eluant:ethyl acetate-hexane, ¼v/v). The fractions containing the product 72 are grouped together and after evaporation of the solvents, a crystalline product is obtained (1.62 g, 54%).

MP: 81°–82° C., $[\alpha]^D{}_{25}=-20°$ (1, chloroform).

Analysis of the infrared spectrum, elementary analysis and analysis of the nuclear magnetic resonance spectrum confirm the structure of the compound 72.

Step 5: synthesis of the derivative 73

Product 72 (2 g) is dissolved in methanol (20 ml) and chloroform (20 ml). To this solution, sodium methanolate is added (2M, 2 ml). After 1.5 hour, the deacetylation reaction is terminated. The reaction mixture is diluted with chloroform. The chloroform phase is washed with water until pH neutral, dried, then evaporated to dryness. In this way a residue is obtained, the compound 72 (1.8 g, 100%). It is immediately dissolved in tetrahydrofuran (50 ml), then boron hydride (BH$_3$, 1M) in tetrahydrofuran; (10 ml) is then added. After one hour of reaction, the excess boron hydride is destroyed by the addition of ethanol. After the gaseous release, the reaction mixture is diluted by the addition of tetrahydrofurane (100 ml). 3M soda (12 ml) is then added, followed by hydrogen peroxide (120 volumes, 8 ml). After 2 hours heating to 50° C., the reaction is stopped. The solution is poured into chloroform (500 ml), then the organic phase so obtained is washed with water, 2M hydrochloric acid, then finally with water until pH neutral. In this way a very milky chloroform phase is obtained, which becomes clear in the course of drying over sodium sulphate. After filtration, the chloroform is evaporated and then the residue obtained is chromatographed on silica (200 g chloroform-methanol, 30/1, v/v).

In this way the iodised derivative is obtained 73 (1.05 g, 55%). This product is in the form of a syrup. $[\alpha]^D{}_{20}=+85.5°$ (1, chloroform).

Elementary analysis as well as NMR analysis confirm the expected structure.

Step 6: synthesis of the derivative 76

This synthesis is carried out from a derivative 73 in a single step (the intermediates 74 and 75 are not isolated). To a solution of the derivative 73 (2.25 g, 6 mM) in dichloromethane (50 ml), are successively added dimethylaminopyridine (60 mg; 0.24 mM) triethylamine (1.7 ml; 12 mM) and trityl chloride (2.5 g; 9 mM). After about 14 hours, the reaction is terminated. In this way the derivative 74 is obtained in solution. Then to the reaction is added dimethylaminopyridine (150 mg), triethylamine (1.7 ml) and benzoyl chloride (1.05 mg). After 6 days, dichloromethane is removed by passage of a flow of nitrogen and replaced by dimethylformamide (40 ml). The reaction mixture is heated to 70° C. overnight. Then benzoyl chloride (1 ml) is again added and trimethylamine (1.7 ml), and then the heating is maintained at 70° C. for 2 days. The dimethylformamide is then evaporated, then the residue is taken up again with chloroform, the chloroform phase is washed with water, with a saturated solution of sodium bicarbonate, then with a 2M hydrochloric acid solution and finally with water until neutral pH. After drying, the chloroform is evaporated, which permits the compound 75 to be obtained.

The latter is immediately subjected to a reaction to remove the trityl group in order to obtain the derivative 76. The residue containing the derivative 75 is dissolved in 25 ml of chloroform and to the solution is added 10 ml of a solution of paratoluenesulphonic acid monohydrate in methanol (1M). After 4 hours of reaction at room temperature, the reaction is terminated. The reaction mixture is then diluted with chloroform, washed with water, dried and then evaporated to dryness. The residue obtained is chromatographed on silica gel (200 g, ether-hexane, 3/1, v/v). The derivative 76 is thus obtained in the pure state (1.5; 52%). This derivative is in the form of a syrup. $[\alpha]^D{}_{20}=-8°$ (1, chloroform).

Analysis of the infrared spectrum and of the NMR spectrum confirm the structure of the expected product.

Step 7: synthesis of the compound 79

This synthesis is carried out directly from the derivative 76 without isolating the intermediates 77 and 78. To the solution of the compound 76 (1.2 g) in acetone (20 ml), is added drop by drop, after cooling to 0° C., a solution of chromium oxide (2.9 ml) (CrO$_3$; 1.17 g) in 3.5M sulphuric acid (5 ml). After 30 minutes stirring at 0° C., the temperature is brought back to room temperature. The reaction develops over 3 hours. The reaction mixture is then poured into a separating funnel containing ice water (100 ml). The product formed is extracted with chloroform (3×50 ml). The chloroform phase is washed with water until pH neutral, then dried over sodium sulphate, filtered and concentrated to dryness. The residue obtained (the compound 77) is dissolved in methanol (130 ml). To this solution 23M soda is added (17 ml) then the mixture is left under stirring for about 14 hours. After acidification with sulphuric acid, the compound 78 is extracted with ether, then immediately methylated with diazomethane according to the conventional method to give the compound 79.

After evaporation with ether, the compound 79 is obtained pure by means of chromatography on silica gel (50 g; ether-hexane; 4/1, v/v). The pure fractions containing the derivative 79 are collected and the solvents are removed. In this way the derivative 79 of iduronic acid is obtained (587 mg, 59% with respect to derivative 76). This product is in the form of a syrup. $[\alpha]^D{}_{25} = +98°$ (2.65, chloroform).

NMR analysis, infrared analysis and elementary analysis confirm the expected structure.

EXAMPLE 20A see FIG. 13

Application of compound 79 to the synthesis of the disaccharide 81

This synthesis is carried out from the monosaccharide 79 prepared as above and from the monosaccharide 80 prepared according to the technique of H. Paulsen and W. Stenzel, Chemische Berichte 111 (1978) 2234–2247.

To a solution of compound 79 (200 mg, 0.5 mM) in dichloromethane (10 ml), is added successively the compound 80 (0.450 g) sym-collidine (150 ul) and silver triflate (260 mg).

The reaction mixture is kept at 0° C. under a flow of nitrogen and with stirring protected from moisture and light for 3 hours.

It is then diluted with dichloromethane (100 ml) and then the solids are removed by filtration on pleated filters. The solution obtained is washed with a saturated solution of sodium bicarbonate with water and with 2M sulphuric acid, then again with water until pH neutral.

After drying over sodium sulphate and evaporation of the dichloromethane, the residue obtained is chromatographed on silica gel (50 g; chloroform/ethyl acetate; 15/1; v/v).

In this way the derivative 81 is obtained pure (327 mg, 82%). The product is in the form of a syrup. $[\alpha]^D{}_{20} = +57°$ (1, chloroform). NMR analysis like elementary analysis confirm the structure and the anomeric nature of the disaccharide 81.

EXAMPLE 21

Synthesis of the triasccharide 85 of formula

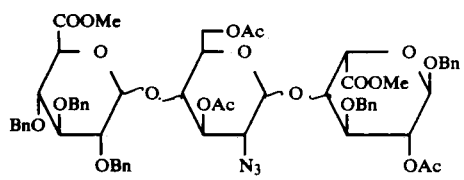

Figure 15:
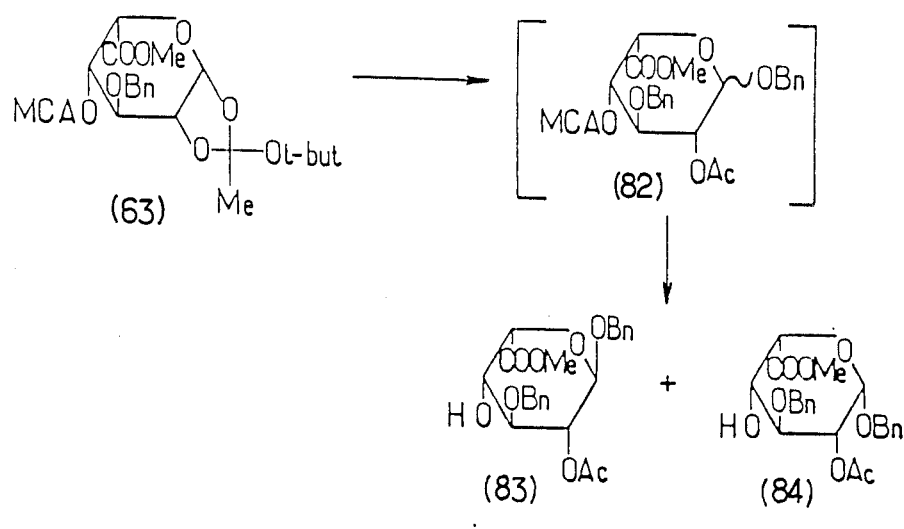
FIG. 15 shows the reactions used in example 21.
Figure 15:
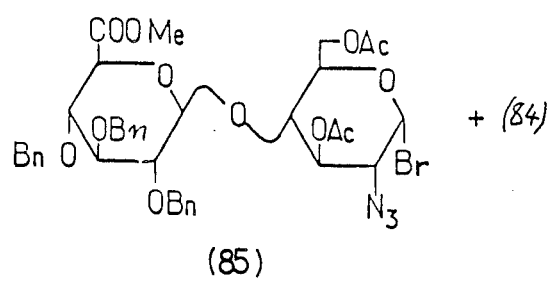
Figure 15:
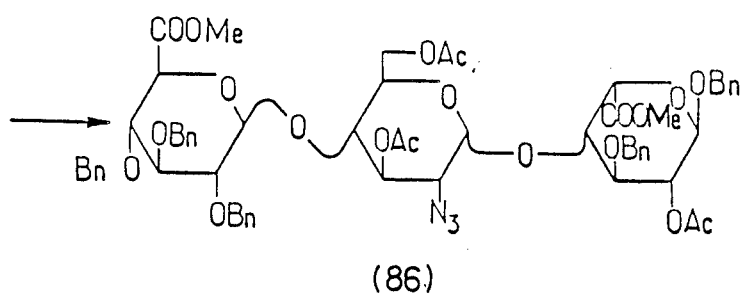

This synthesis is carried in 3 steps (see FIG. 15). Firstly, the glycosylation of the orthoester of a derivative of L-iduronic acid is carried out. Then selectively the monochloroacetyl group is removed, then one of the alcohols formed is reacted with a disaccharide.

(1)—Glycosylation of the orthoester 63 with benzyl alcohol

A solution of the orthoester 63 (118 mg 0.25 mM) obtained as described above and of benzyl alcohol (0.15 ml, 15 mM, freshly distilled) in anhydrous chlorobenzene (10 ml) is heated to 140° C. protected from moisture. After slow distillation of 8 ml of solvent, a solution of 2.6-dimethylpyridinium perchlorate (2.5 μM) in chlorobenzene (2 ml) is added drop by drop in 30 min with simultaneous distillation of solvent (2 ml). The reaction mixture is then stirred 30 min under these conditions, with the addition drop by drop of fresh solvent and simultaneous distillation, so that the reaction volume remains constant and equal to 2 ml. After cooling and dilution with chloroform (50 ml), the organic phase is washed with an aqueous 5% sodium hydrogenocarbonate solution, with water, dried (sodium sulphate) filtered and evaporated. The residue is chromatographed over column of silica gel (8 g). Elution with the mixture hexane-ethyl acetate (2:1, v/v) enabled a fraction to be obtained containing the mixture 82 of α and β glycosides which have not been separated at this stage (102 mg, 81%), N.M.R. (90 MH$_z$, CDCl$_3$): ;7.30 (m, 10 H, 2 Ph), 3.98 (s, 2 H, Cl—CH Cl—CH$_2$—CO), 3.74 (s, 3H, COOMe), 2.08 and 2.03 (2 s, 3 H in total, OAc form α and β; βα≃2:1).

(2)—Selective O-demonchloroacetylation

A solution of the preceding mixture 82 (102 mg) in pyridine (5 ml) and absolute ethanol (1 ml) is heated to 100° C. for 20 min. in the presence of thiourea (25 mg). After cooling, the reaction mixture is evaporated to dryness and the residue is taken up again by a water-chloroform mixture (1:1. v/v, 50 ml). The organic phase is washed with water, dried (sodium sulphate), filtered and evaporated.

The residue is chromatographed on a silica gel column (10 g). Elution with the mixture ethyl-acetate-hexane (4:3, v/v) enables isolation (in order of elution):

The β glycoside 83 (26 mg, 25%), colourless syrup, $[\alpha]_D + 70°$ )c, chloroform), N.M.R. (90 MH$_x$, CdCl$_3$):δ7.30 (m, 10 H, 2 Ph); 5.05 (m, 1 H, H$_2$)l 4.90 (d, 1 H, H$_1$, 1.2 J=2 H$_z$); 3.78 (s, 3 H, COOMe); 3.12 (1 H, OH, exchange with D$_2$O); 2.05 (s, 3 H, OAc).

the α glycoside 84 (54 mg, 50% from 63) colourless syrup, $[\alpha]_D - 65°$ (c1, chloroform), N.M.R. (90 MH$_z$, CdCl$_3$):δ:7.30 (m, 10 H, 2 Ph); 5.05 (2 H, H$_1$ and H$_2$, very weak coupling constants for J$_{1,2}$ ≦ 1 Hz); 3.78 (s, 3 H, COOMe); 2.80 (1 H, OHexchanged with D$_2$O); 2.06 (s, 3 H, OAc).

(3)—Glycosylation of the alcohol 84 by means of the disaccharide 85

A solution of the alcohol 84 (22 mg, 50 μM), and of bromide 85 (57 mg, 70 μM) in anhydrous dichloromethane (1.5 ml) is stirred protected from light and moisture in the presence of 4 Å molecular sieve (powder 50 mg). The reaction mixture is cooled to −20° C. and sym-collidine (110 μl) and silver triflate (26 mg, 100 μM) are added successively. The reaction mixture is stirred 1 h under these conditions, diluted with dichloromethane (50 ml) the solids are drained and the filtrate is washed with an icy aqueous solution of 0.1 M, HCl, with water, with an aqueous 5% solution of sodium hydrogenocarbonate, with water, dried (sodium sulphate), filtered and evaporated.

The residue is chromatographed on a silica gel column (8 g, gel 230–400 mesh). Elution by the mixture tolueneethyl acetate (5:1, v/v) enabled isolation of the trisaccharide 86 in the form of a colourless syrup (50 mg, 86%).

The N.M.R. spectrum (270 MH$_z$ CDCl$_3$) agrees with the expected structure.

Figure 16:
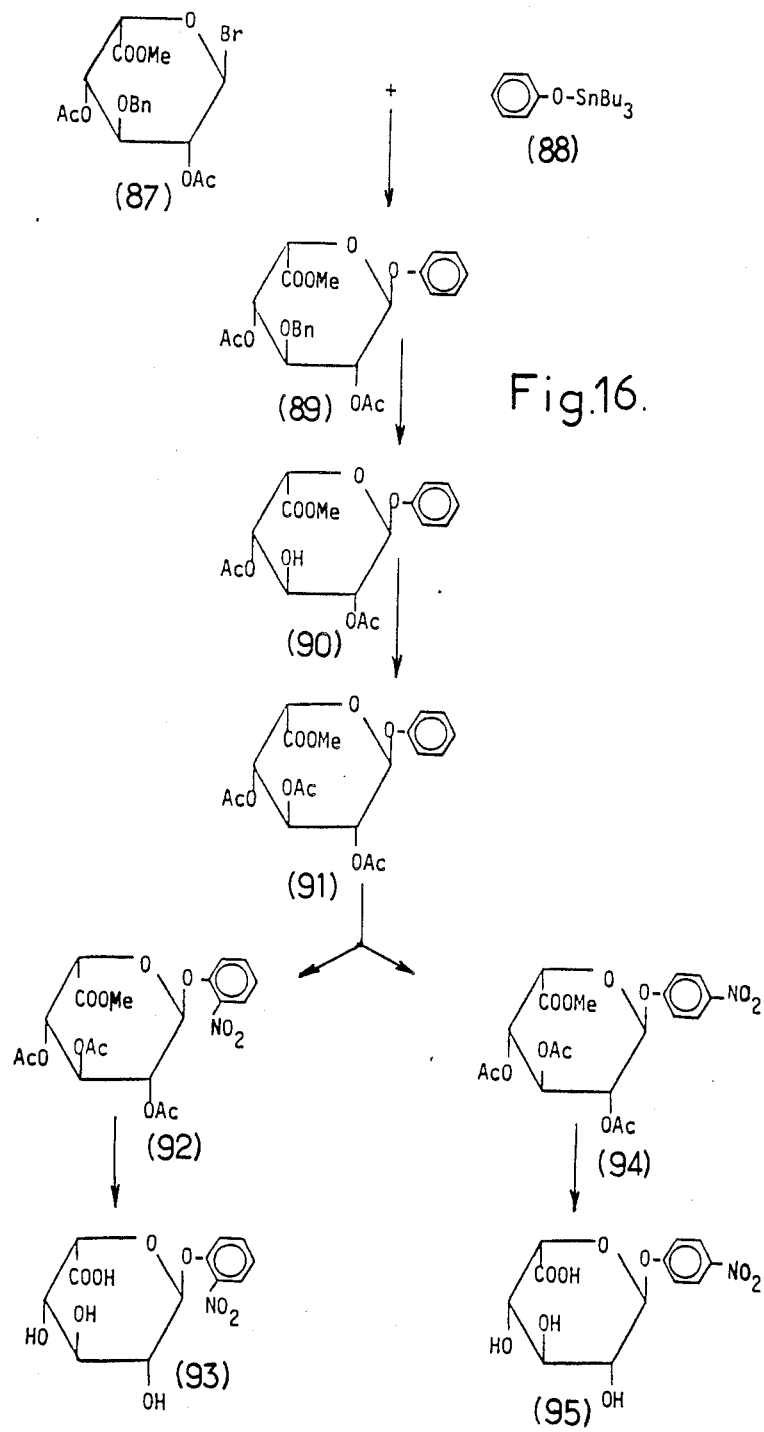
FIG. 16 shows the use of a uronic acid according to the invention for making enzyme substrates. The reference numerals used in these Figures to denote the derivatives are also taken up again in the Examples. In these Figures the symbols used have the following meanings: A represents an allyl group, by —C6H5 group, Bn a benzyl group, Tr a trityl group, R6 a —OAc or —OBz group, with Ac representing an acetyl group and Bz a benzoyl group, Me a methyl group, P a vinyl group and MCA a monochloroacetyl group, Tf a triflyl group, t-Bu a tertiobultyl group and SnBu$_3$ the tributyl stanyl radical.

EXAMPLE 22 see FIG. 16

Application of the L-iduronic acid derivative 87 the formula:

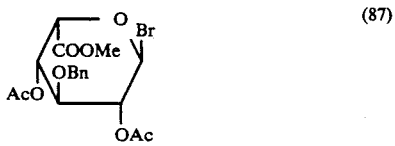 (87)

for synthesizing glycosides useful as enzyme substrates of the formula:

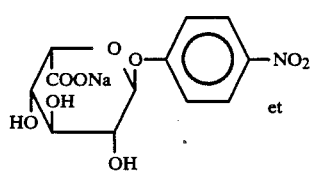 et

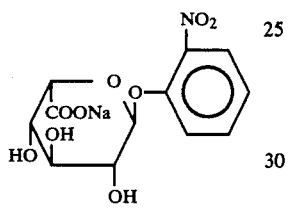

Synthesis of Compound 87

The compound 87 (French patent application No. 82 01575; 900 mg; 2 mmoles) is dissolved in dichloroethane (20 ml). Then tributyl Stannyl Phenol (88; 2.5 μmoles) is added and then stannic chloride (2.5 mmoles). After 5 hours, the reaction mixture is diluted with dichloromethane, washed with a sodium bicarbonate solution, then with water. The residue obtained after drying and evaporation of the solvents (1.03 g) is directly hydrogenated. For this, it is dissolved in methanol, then the solution is stirred under a hydrogen atmosphere in the presence of Pd/C (5%; 0.5 g) for 3 hours. The catalyst is then removed by filtration and then the solution is concentrated to dryness. The residue is acetylated by acetic anhydride in the presence of pyridine, thus releasing 89 (420 mg) purified on a silica gel column (100 g; Ether/hexane; 3/1; v/v). The NMR spectrum and elementary analysis confirm the structure of 89.

Synthesis of Compounds 93 and 95

To a solution of 89 (400 mg) dissolved in glacial acetic acid (2.5 ml) is added drop by drop, with stirring and at 0° C., a mixture (1 ml) constituted by acetic anhydride (16 volumes) and nitric acid (5 volumes). After two hours at 35° C., the reaction mixture is poured into ice water and then the products formed (90 and 91) are extracted with chloroform. The chloroform phase is washed with 5% bicarbonate in water, dried and then concentrated to dryness. The products 90 and 91 formed in a ratio of about 2/1, are separated by chromatography on silica gel (25 g; ether/hexane, 1/1, v/v). In this way is obtained a pure 90 (10 mg), pure 91 (19 mg) and a fraction containing both 90 and 91, unseparated.

92 and 94 are dissolved in methanol at 0° C. 4N soda is added drop by drop until basis pH. When hydrolysis is complete Dowex resin 50 H+ is added so as to deionise the solution. After freeze-drying, the compounds 93 (11 mg) and 95 (10 mg) are obtained. Their NMR spectra confirm their structures.

It will be noted that various substituents can be introduced on the glycosides 89 after the condensation step.

The protective groups can be for example removed all together or successively from either positions 2 and-/or 3 and/or 4, and specific substituents can then be introduced, for example a —SO₃ group enabling the preparation of a lot of various glycosides.

Other glycosides were also prepared by using L-iduronic acid and D-glucuronic acid derivatives comprising substituents different from those of derivative 89.

We claim:

1. A compound having the following formula:

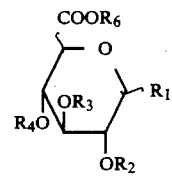

wherein
a. R₁ is selected from group consisting of
  i. Br,
  ii. Cl,
  iii. —O— imidoyl,
  iv. —O-allyl,
  v. —O-vinyl,
  vi. —OCH₃,
  vii. —O—C₆H₅,
  viii. —O—CO—CH₃,
  Xi. —OH,
  x. an orthoester which together with —OR₂ forms —OH(CH₃)(OtBu)O—,
  xi. an orthoester which together with —OR₂ forms —OC(CH₃)(OCH₃)O—, and
  xii. —O-nitrophenyl;
b. R₂ is selected from the group consisting of
  i. methyl,
  ii. benzyl,
  iii. acetyl,
  iv. benzoyl,
  v. chloroacetyl,
  vi. allyl,
  vii. vinyl,
  viii. an orthoester which together with —OR₁ forms —OC(CH₃)(OtBu)O—, and
  ix. an orthoester which together with —OR₁ forms —OC(CH₃)(OCH₃)O—;
c. R₃ is selected from the group consisting of
  i. methyl,
  ii. benzyl,
  iii. acetyl,
  iv. benzoyl,
  v. chloroacetyl,
  vi. allyl, and
  vii. vinyl;
d. R₄ is selected from the group consisting of
  i. methyl,
  ii. benzyl,
  iii. acetyl,
  iv. benzoyl,
  v. chloroacetyl,
  vi. allyl,
  vii. vinyl, and viii. paramethoxy benzyl;
e. R$_6$ is selected from the group consisting of
  i. methyl,
  ii. benzoyl, and
  iii. a cation of a pharmaceutically acceptable salt;
provided that
  where R$_1$ is a methoxy group, R$_4$ is not methyl,
  where COOR$_6$ is in the glucuronic position, R$_2$, R$_3$, and R$_4$ are not identical,
  where R$_1$ and R$_2$ form an orthoester, R$_3$ and R$_4$ are not acetyl,
  at least one of R$_2$ or R$_3$ is acetyl.

2. A compound having the following formula:

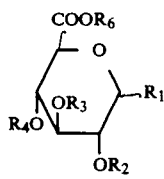

wherein
a. R$_1$ is selected from group consisting of
  i. —O-allyl,
  ii. —O-vinyl, and
  iii. —OH;
b. R$_2$ is selected from the group consisting of
  i. methyl,
  ii. benzyl,
  iii. acetyl,
  iv. benzoyl,
  v. chloroacetyle,
  vi. allyl,
  vii. vinyl,
  viii. or orthoester which together with —OR$_1$ forms —OC(CH$_3$)(OtBu)O—, and
  ix. an orthoester which together with —OR$_1$ forms —OC(CH$_3$(OCH$_3$)O—;
c. R$_3$ is selected from the group consisting of
  i. methyl,
  ii. benzyl,
  iii. acetyl,
  iv. benzoyl,
  v. chloroacetyl,
  vi. allyl, and
  vii. vinyl;
d. R$_4$ is selected from the group consisting of
  i. monochloroacetyl,
  ii. acetyl,
  iii. benzyl,
  vi. p-methoxybenzyl,
  v. allyl, and
  vi. vinyl;
e. R$_6$ is selected from the group consisting of
  i. methyl,
  ii. benzyl, and
  iii. a cation of a pharmaceutically acceptable salt;
provided that
  where COOR$_6$ is in the glucuronic position, R$_2$, R$_3$, and R$_4$ are not identical
  where R$_1$ and R$_2$ form an orthoester, R$_3$ and R$_4$ are not acetyl.

3. A compound having the following formula:

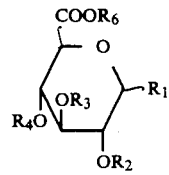

wherein
a. R$_1$ is —OH;
b. R$_2$ is selected from the group consisting of
  i. methyl,
  ii. benzyl,
  iii. acetyl,
  iv. benzoyl,
  v. chloroacetyl,
  vi. allyl,
  vii. vinyl,
  viii. an orthoester which together with —OR$_1$ forms —OC(CH$_3$)(OtBu)O—, and
  ix. an orthoester which together with —OR$_1$ forms —OC(CH$_3$)(OCH$_3$)O—;
c. R$_3$ is selected from the group consisting of
  i. methyl,
  ii. benzyl,
  iii. acetyl,
  iv. benzoyl,
  v. chloroacetyl,
  vi. allyl, and
  vii. vinyl;
d. R$_4$ is selected from the group consisting of
  i. methyl,
  ii. benzyl,
  iii. acetyl,
  iv. benzoyl,
  v. chloroacetyl,
  vi. allyl,
  vii. vinyl, and
  viii. paramethoxy benzyl;
e. R$_6$ is selected from the group consisting of
  i. methyl,
  ii. benzoyl, and
  iii. a cation of a pharmaceutically acceptable salt;
provided that
  where COOR$_6$ is in the glucuronic position, R$_2$, R$_3$, and R$_4$ are not identical.

4. A compound according to claim 1, wherein R$_1$ is —OH.

5. A compound having the following formula

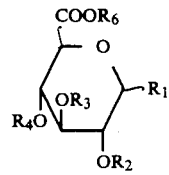

wherein
a. R$_1$ is —O-allyl;
b. R$_2$ is selected from the group consisting of
  i. methyl,
  ii. benzyl,
  iii. acetyl,
  iv. benzoyl,
  v. chloroacetyl,
  vi. allyl, vii. vinyl,
viii. an orthoester which together with —OR$_1$ forms —OC(CH$_3$)(OtBu)O—, and
ix. an orthoester which together with —OR$_1$ forms —OC(CH$_3$)(OCH$_3$)O—;
c. R$_3$ is selected from the group consisting of
  i. methyl,
  ii. benzyl,
  iii. acetyl,
  iv. benzoyl,
  v. chloroacetyl,
  vi. allyl, and
  vii. vinyl;
d. R$_4$ is —OH;
e. R$_6$ is selected from the group consisting of
  i. methyl,
  ii. benzyl, and
  iii. a cation of a pharmaceutically acceptable salt.
6. A compound according to claim 1, wherein R$_4$ is —OH, and R$_1$ is —O-allyl.

* * * * *

UNITED STATES PATENT AND TRADEMARK OFFICE
CERTIFICATE OF CORRECTION

PATENT NO. : 4,987,223

DATED : January 22, 1991

INVENTOR(S) : Choay, et al.

It is certified that error appears in the above-identified patent and that said Letters Patent is hereby corrected as shown below:

The following should be added to the title page:

--[30] Foreign Application Priority Data
    April 28, 1982 [EPA] European Patent.........82400770.2--.

Signed and Sealed this

Sixteenth Day of March, 1993

Attest:

STEPHEN G. KUNIN

*Attesting Officer*     Acting Commissioner of Patents and Trademarks